(12) United States Patent
Barnes

(10) Patent No.: US 10,010,458 B2
(45) Date of Patent: Jul. 3, 2018

(54) ELASTIC COMPOSITE AND ABSORBENT ARTICLE INCLUDING THE SAME

(71) Applicant: Kimberly-Clark Worldwide, Inc., Neenah, WI (US)

(72) Inventor: Nickolas Barnes, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/127,947

(22) PCT Filed: Aug. 31, 2015

(86) PCT No.: PCT/US2015/047672
§ 371 (c)(1),
(2) Date: Sep. 21, 2016

(87) PCT Pub. No.: WO2017/039599
PCT Pub. Date: Mar. 9, 2017

(65) Prior Publication Data
US 2017/0231835 A1    Aug. 17, 2017

(51) Int. Cl.
*A61F 13/00* (2006.01)
*A61F 13/49* (2006.01)
*A61F 13/495* (2006.01)

(52) U.S. Cl.
CPC ........ *A61F 13/4902* (2013.01); *A61F 13/495* (2013.01); *A61F 13/49011* (2013.01); *A61F 13/49014* (2013.01); *A61F 13/49017* (2013.01)

(58) Field of Classification Search
CPC ............ A61F 13/4902; A61F 13/49011; A61F 13/49014; A61F 13/49017; A61F 13/495
See application file for complete search history.

(56) References Cited

U.S. PATENT DOCUMENTS

| | | | |
|---|---|---|---|
| 3,395,708 | A | 8/1968 | Hervey et al. |
| 3,930,501 | A | 1/1976 | Schaar |
| 3,978,861 | A | 9/1976 | Schaar |
| 3,995,640 | A | 12/1976 | Schaar |
| 4,525,407 | A | 6/1985 | Ness |

(Continued)

FOREIGN PATENT DOCUMENTS

| | | |
|---|---|---|
| JP | 2001-178772 A | 7/2001 |
| JP | 4754634 B2 | 8/2011 |

(Continued)

*Primary Examiner* — Adam Marcetich
*Assistant Examiner* — Jessica Arble
(74) *Attorney, Agent, or Firm* — Kimberly-Clark Worldwide, Inc.

(57) ABSTRACT

An elastic composite (10, 110, 210, 310) can include a first layer (20, 120, 220, 320), a second layer (22, 122, 222, 322), and a third layer (24, 124, 224, 324). The third layer (24, 124, 224, 324) can be formed by at least one elastic material (32, 132, 232, 332) and can be coupled to the second layer (22, 122, 222, 322) when the elastic material (32, 132, 232, 332) is in an extended condition. The first layer (20, 120, 220, 320) can be coupled to the second layer (22, 122, 222, 322) near the first and second longitudinal edge (16, 18) but can be independent of the second layer (22, 122, 222, 322) therebetween such that the first layer (20, 120, 220, 320) forms gathers (36, 136, 236, 336) when the elastic composite (10, 110, 210, 310) is in a retracted condition.

16 Claims, 10 Drawing Sheets

(56) References Cited

U.S. PATENT DOCUMENTS

| | | |
|---|---|---|
| 4,657,539 A | 4/1987 | Hasse |
| 4,657,802 A | 4/1987 | Morman |
| 4,681,579 A | 7/1987 | Toussant et al. |
| 4,738,677 A | 4/1988 | Foreman |
| 4,741,949 A | 5/1988 | Morman et al. |
| 4,753,646 A | 6/1988 | Enloe |
| 4,808,176 A | 2/1989 | Kielpikowski |
| 4,808,177 A | 2/1989 | Desmarais et al. |
| 4,822,435 A | 4/1989 | Igaue et al. |
| 4,850,990 A | 7/1989 | Huntoon et al. |
| 4,938,755 A | 7/1990 | Foreman |
| 4,977,011 A | 12/1990 | Smith |
| 5,026,364 A | 6/1991 | Robertson |
| 5,064,421 A | 11/1991 | Tracy |
| 5,069,672 A | 12/1991 | Wippler et al. |
| 5,106,385 A | 4/1992 | Allen et al. |
| 5,151,092 A | 9/1992 | Buell et al. |
| 5,187,817 A | 2/1993 | Zolner |
| 5,209,801 A | 5/1993 | Smith |
| 5,397,318 A | 3/1995 | Dreier |
| 5,413,570 A | 5/1995 | Enloe |
| 5,439,459 A | 8/1995 | Tanji et al. |
| 5,514,121 A | 5/1996 | Roe et al. |
| 5,531,730 A | 7/1996 | Dreier |
| 5,540,671 A | 7/1996 | Dreier |
| 5,558,660 A | 9/1996 | Dreier |
| 5,558,661 A | 9/1996 | Roe et al. |
| 5,569,227 A | 10/1996 | Vandemoortele et al. |
| 5,582,606 A | 12/1996 | Bruemmer et al. |
| 5,593,401 A | 1/1997 | Sosalla et al. |
| 5,649,918 A | 7/1997 | Schleinz |
| 5,667,503 A | 9/1997 | Roe et al. |
| 5,672,166 A | 9/1997 | Vandemoortele |
| 5,674,215 A | 10/1997 | Roennberg |
| 5,690,627 A | 11/1997 | Clear et al. |
| 5,695,488 A | 12/1997 | Sosalla |
| 5,776,121 A | 7/1998 | Roe et al. |
| 5,817,086 A | 10/1998 | Kling |
| 5,827,259 A | 10/1998 | Laux et al. |
| 5,895,382 A | 4/1999 | Popp et al. |
| 5,904,675 A | 5/1999 | Laux et al. |
| 5,931,826 A | 8/1999 | Faulks et al. |
| 5,938,652 A | 8/1999 | Sauer |
| 5,993,433 A | 11/1999 | St. Louis et al. |
| 6,103,952 A | 8/2000 | Coles et al. |
| 6,135,988 A | 10/2000 | Turner et al. |
| 6,142,985 A | 11/2000 | Feist |
| 6,149,638 A | 11/2000 | Vogt et al. |
| 6,217,563 B1 | 4/2001 | Gompel et al. |
| 6,258,076 B1 | 7/2001 | Glaug et al. |
| 6,264,639 B1 | 7/2001 | Sauer |
| 6,280,426 B1 | 8/2001 | Turner et al. |
| 6,293,937 B2 | 9/2001 | Matsushita et al. |
| 6,306,122 B1 | 10/2001 | Narawa et al. |
| 6,315,764 B1 | 11/2001 | Faulks et al. |
| 6,425,889 B1 | 7/2002 | Kitaoka et al. |
| 6,443,933 B1 | 9/2002 | Suzuki et al. |
| 6,455,753 B1 | 9/2002 | Glaug et al. |
| 6,458,114 B1 | 10/2002 | Mishima et al. |
| 6,482,194 B1 | 11/2002 | Putzer |
| 6,491,677 B1 | 12/2002 | Glaug et al. |
| 6,494,872 B1 | 12/2002 | Suzuki et al. |
| 6,506,185 B1 | 1/2003 | Sauer et al. |
| 6,527,756 B1 | 3/2003 | Mishima et al. |
| 6,638,262 B2 | 10/2003 | Suzuki et al. |
| 6,699,228 B1 | 3/2004 | Chmielewski et al. |
| 6,827,806 B2 | 12/2004 | Uitenbroek et al. |
| 6,838,591 B2 | 1/2005 | Waksmundzki et al. |
| 6,881,207 B1 | 4/2005 | Tracy |
| 6,890,327 B2 | 5/2005 | Suzuki et al. |
| 7,066,921 B2 | 6/2006 | Schmoker et al. |
| 7,166,095 B1 | 1/2007 | Coates |
| 7,247,152 B2 | 7/2007 | Klemp et al. |
| 7,604,625 B2 | 10/2009 | Turi et al. |
| 7,666,173 B2 | 2/2010 | Mishima et al. |
| 7,767,876 B2 * | 8/2010 | Davis ..................... A61F 13/15 206/458 |
| 7,842,021 B2 | 11/2010 | Wood et al. |
| 7,879,017 B1 | 2/2011 | Tabata et al. |
| 7,993,314 B2 | 8/2011 | Asp et al. |
| 8,075,543 B2 | 12/2011 | Okuda |
| 2001/0016720 A1 | 8/2001 | Otsubo |
| 2002/0082570 A1 | 6/2002 | Mishima et al. |
| 2002/0147438 A1 | 10/2002 | Tanaka et al. |
| 2003/0045853 A1 | 3/2003 | Sauer |
| 2003/0050616 A1 | 3/2003 | Reynolds et al. |
| 2004/0002690 A1 | 1/2004 | Miyamoto |
| 2004/0019343 A1 | 1/2004 | Olson et al. |
| 2004/0127882 A1 | 7/2004 | Weber |
| 2004/0243086 A1 | 12/2004 | VanGompel et al. |
| 2005/0027274 A1 | 2/2005 | Suzuki et al. |
| 2005/0148974 A1 | 7/2005 | Datta et al. |
| 2005/0215974 A1 * | 9/2005 | O'Connell ........ A61F 13/15723 604/392 |
| 2006/0058738 A1 | 3/2006 | Ponzi et al. |
| 2006/0058767 A1 | 3/2006 | Zhang et al. |
| 2007/0112322 A1 | 5/2007 | Ashton et al. |
| 2007/0293832 A1 | 12/2007 | Wood et al. |
| 2012/0277703 A1 | 11/2012 | Rhein et al. |
| 2013/0012905 A1 | 1/2013 | Katsuragawa et al. |
| 2013/0012907 A1 | 1/2013 | Sasayama et al. |
| 2013/0046266 A1 | 2/2013 | Kawakami |
| 2014/0121623 A1 | 5/2014 | Kirby et al. |
| 2014/0128829 A1 | 5/2014 | Miyake et al. |
| 2014/0257231 A1 * | 9/2014 | Wang .................... A61F 13/514 604/394 |
| 2014/0350504 A1 | 11/2014 | Popp et al. |
| 2015/0182388 A1 | 7/2015 | Katsuragawa et al. |
| 2017/0000658 A1 | 1/2017 | Chatterjee et al. |
| 2017/0128281 A1 | 5/2017 | Takino et al. |
| 2017/0246055 A1 | 8/2017 | Barnes |

FOREIGN PATENT DOCUMENTS

| | | |
|---|---|---|
| KR | 10-0648562 B1 | 11/2006 |
| WO | WO 2016/159983 A1 | 10/2016 |

* cited by examiner

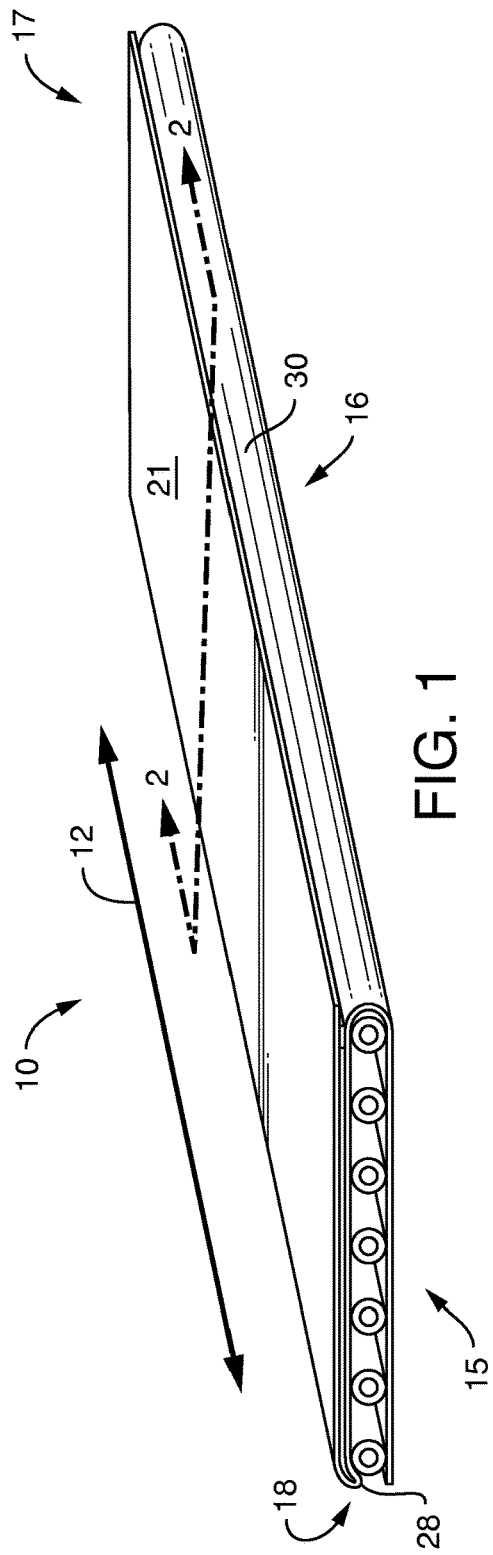
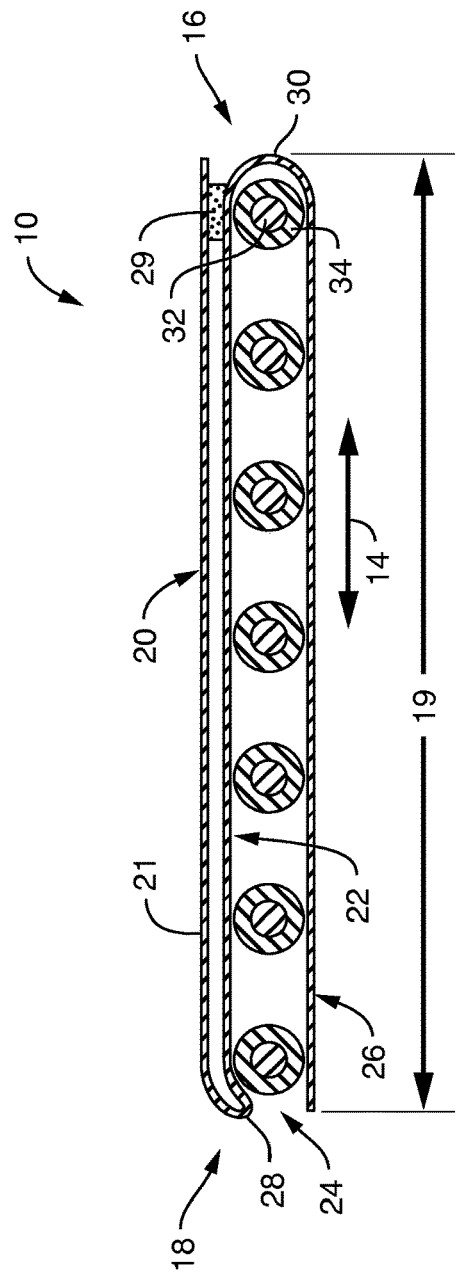
FIG. 1
FIG. 2

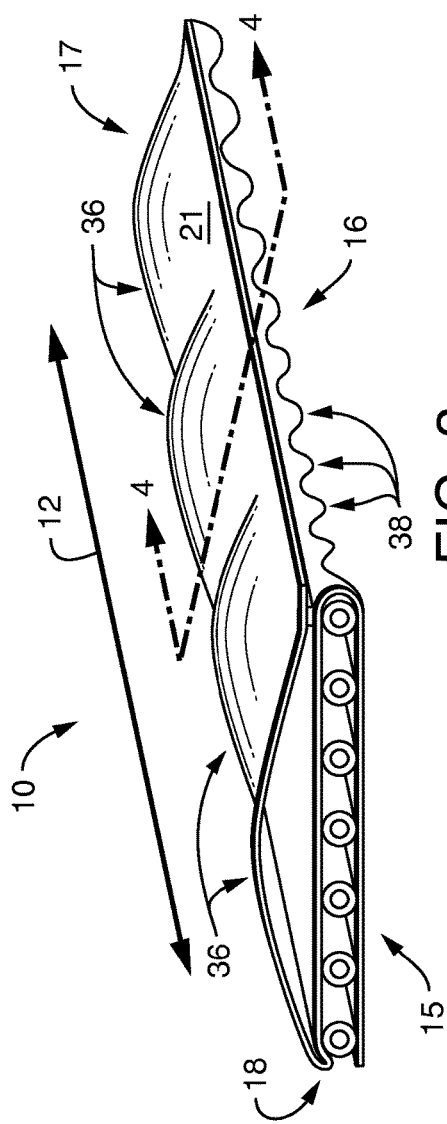
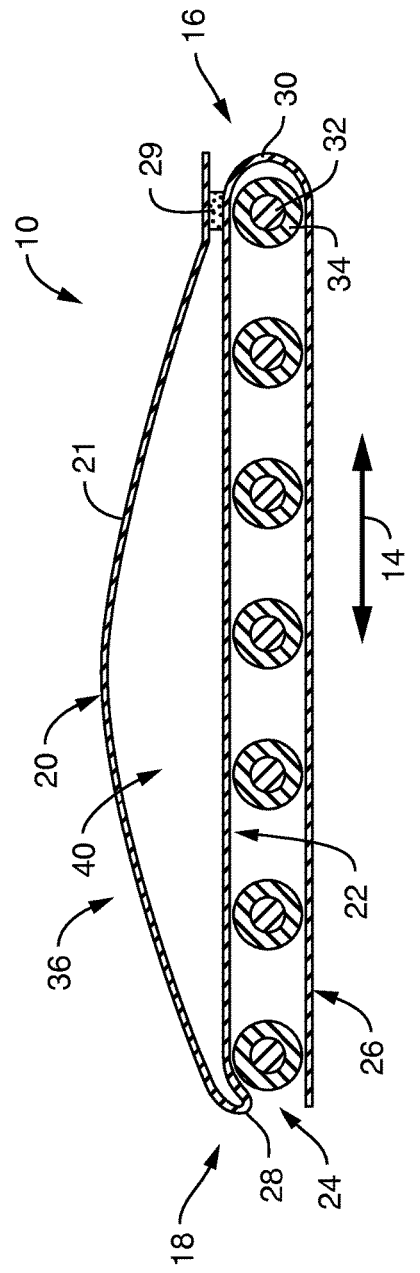
FIG. 3
FIG. 4

ELASTIC COMPOSITE AND ABSORBENT ARTICLE INCLUDING THE SAME

TECHNICAL FIELD

The present disclosure relates to elastic composites and absorbent articles including elastic composites.

BACKGROUND OF THE DISCLOSURE

Various articles employ elastic materials for purposes of fit and to provide specific functional benefits. For example, some absorbent articles such as diapers and pants, utilize elastic materials to provide a better fit for the wearer around the legs and waist. Absorbent articles also utilize elastic materials to provide gasketing for exudates, for example, in leg containment flaps. Other types of articles, such as clothing, coveralls, workwear, athletic apparel, surgical gowns, etc., can also utilize elastic material to achieve proper fit and/or function.

However, elastic materials can also serve as a potential source of irritation against the skin of a wearer. While such irritation can be reduced by providing thicker and softer facing materials over the elastic materials, covering the elastic materials in such a fashion can be costly. Additionally, the construction of some elastic composites provides facing materials of limited topography, or micro-topography that may go unnoticed by the user and/or wearer. By having minimal changes in topography, these elastic composites do not provide the appearance of softness to the user and/or wearer, or in the context of some absorbent articles, to a caregiver.

Thus, there is a desire for improvements to elastic composites to provide increased softness as well as the perception of increased softness. There is also a desire for improvements to absorbent articles including elastic composites to provide increased softness as well as the perception of increased softness.

SUMMARY OF THE DISCLOSURE

In one embodiment, elastic composite can include an elastic composite longitudinal axis and an elastic composite lateral axis. The elastic composite can include a first longitudinal edge and a second longitudinal edge. The first longitudinal edge and the second longitudinal edge can each extend in a direction generally parallel to the elastic composite longitudinal axis. The elastic composite can further include a first layer formed by at least one facing material. The elastic composite can also include a second layer formed by at least one facing material. The elastic composite can additionally include a third layer formed by at least one elastic material. The third layer can be coupled to the second layer when the at least one elastic material is in an extended condition and the first layer can be coupled to the second layer near the first longitudinal edge and the second longitudinal edge but can be independent of the second layer therebetween such that when the elastic composite is in a retracted condition the first layer forms gathers in the direction parallel to the elastic composite longitudinal axis.

In another embodiment, an absorbent article can include a front waist region, a rear waist region, a crotch region. The absorbent article can include an article longitudinal axis and an article lateral axis. The absorbent article can include a chassis including an absorbent body. The chassis can include a body facing surface. The absorbent article can further include an elastic composite. The elastic composite can include an elastic composite longitudinal axis and an elastic composite lateral axis, and a first longitudinal edge and a second longitudinal edge. The first longitudinal edge and the second longitudinal edge can each extend in a direction generally parallel to the elastic composite longitudinal axis. The elastic composite can further include a first layer formed by at least one facing material. The elastic composite can further include a second layer formed by at least one facing material. Furthermore, the elastic composite can include a third layer formed by at least one elastic material. The third layer can be coupled to the second layer when the at least one elastic material is in an extended condition. The first layer can be coupled to the second layer near the first longitudinal edge and the second longitudinal edge but can be independent of the second layer therebetween such that when the elastic composite is in a retracted condition the first layer forms gathers in the direction parallel to the longitudinal axis.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 1 is a top, side perspective view of an exemplary embodiment of an elastic composite, the elastic composite being in an extended configuration.

FIG. 2 is a cross-sectional view taken along line 2-2 from FIG. 1.

FIG. 3 is a top, side perspective view of the elastic composite of FIG. 1, the elastic composite being in a retracted configuration.

FIG. 4 is a cross-sectional view taken along line 4-4 from FIG. 3.

Figure 5A:
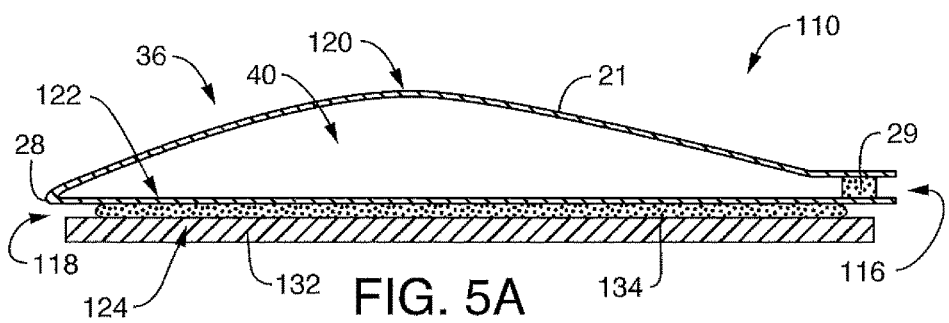
FIG. 5A is a cross-sectional view similar to FIG. 4, but of an alternative embodiment of an elastic composite in a retracted configuration.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an elastic composite 10, 110, 210, 310 and an absorbent article 50, 150, 250 that includes at least one elastic composite 10, 110, 210, 310. The elastic composite 10, 110, 210, 310 can provide the benefits of additional softness as well as the appearance of softness. Among other potential uses, the absorbent article 50, 150 can include an elastic composite 10, 110, 210, 310 that forms a waist containment member 84, and/or a leg containment flap 80, 82, and/or a side panel 95a, 95b, 96a, 96b. As noted herein, the elastic composite 10, 110, 210, 310 are not limited to use in absorbent articles, and can be used in various other articles. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Elastic Composite:

Referring to FIGS. 1-4, an elastic composite 10 is illustrated. The elastic composite 10 can include an elastic composite longitudinal axis 12 (as labeled in FIG. 1) and an elastic composite lateral axis 14 (as labeled in FIG. 2). The elastic composite 10 can include a first longitudinal edge 16 and a second longitudinal edge 18. The first longitudinal edge 16 and the second longitudinal edge 18 can each extend in a direction parallel to the elastic composite longitudinal axis 12. A width 19 of the elastic composite 10 can be defined between the first longitudinal edge 16 and the second longitudinal edge 18 when the elastic composite is in the extended condition, as illustrated in FIG. 2. The elastic composite 10 can also include a first end 15 and a second end 17, as labeled in FIGS. 1 and 4.

In the embodiment illustrated in FIGS. 1-4, the elastic composite 10 can include a first layer 20, a second layer 22, a third layer 24, and a fourth layer 26. The first layer 20 can be formed by at least one facing material. The first layer 20 can provide an outer surface 21 for the elastic composite 10. The second layer 22 can be formed by at least one facing material, and the fourth layer 26 can be formed by at least one facing material. In some embodiments, the first layer 20, the second layer 22, and the fourth layer 26 can all be formed by the same facing material. In some embodiments, such as illustrated in FIGS. 1-4, the elastic composite 10 can be configured such that the first layer 20 is directly coupled to the second layer 22 at the second longitudinal edge 18 by a fold 28. The second layer 22 can be directly coupled to the fourth layer 26 at the first longitudinal edge 16 by a fold 30. The first layer 20 can be coupled to the second layer 22 at the first longitudinal edge 16 with adhesive 29 (as shown in FIGS. 2 and 4). The adhesive 29 can be applied to either or both the first layer 20 or the second layer 22. The first layer 20 is coupled to the second layer 22 at the first longitudinal edge 16 in the direction of the elastic composite longitudinal axis 12. In a preferred embodiment, the first layer 20 is coupled to the second layer 22 at the first longitudinal edge 16 in the direction of the elastic composite longitudinal axis 12 in a continuous fashion from the first end 15 to the second end 17 via adhesive 29, however, it is contemplated that the first layer 20 could be coupled to the second layer 22 at the first longitudinal edge 16 in the direction of the elastic composite longitudinal axis 12 in an intermittent fashion.

The third layer 24 of the elastic composite 10 can be formed by at least one elastic material 32. For example, the elastic composite 10 depicted in FIGS. 1-4 includes seven elastic materials 32 (only one being labeled in FIGS. 2 and 4 for purposes of clarity), such as elastic strands, that form the third layer 24. Of course, it is contemplated that the third layer 24 can be formed by other amounts of elastic materials 32 other than seven and still be within the spirit of this disclosure. The third layer 24 can be disposed between the second layer 22 and the fourth layer 26. The third layer 24 can be coupled to the second layer 22 and the fourth layer 26 via an adhesive 32, (only one adhesive 32 being labeled in FIGS. 2 and 4 for purposes of clarity).

It is to be appreciated that although an adhesive 29 is used to couple the first layer 20 to the second layer 22 at the first longitudinal edge 16 and an adhesive 32 is used to couple the elastic material 32 of the third layer 24 to the second layer 22 and the fourth layer 26 in the elastic composite 10 depicted in FIGS. 1-4, it is contemplated that any other suitable bonding method, including, but not limited to, pressure bonding, ultrasonic bonding, heat fusion bonding, stitching, or any combinations thereof could be used and still be within the spirit of this disclosure.

The third layer 24 can be coupled to the second layer 22 when the elastic material 32 is in an extended condition, which is shown in FIGS. 1 and 2. By coupling the third layer 24 to the second layer 22 when the elastic material 32 is in an extended condition, the elastic properties of the third layer 24 can be transferred to the remainder of the elastic composite 10. As best illustrated in FIGS. 2 and 4, the first layer 20 is independent of the second layer 22 between the first longitudinal edge 16 and the second longitudinal edge 18. Although the adhesive 29 coupling the first layer 20 to the second layer 22 at the first longitudinal edge 16 has some lateral width in a direction of the elastic composite lateral axis 14, the first layer 20 is referred to herein as being independent of the second layer 22 between the first longitudinal edge 16 and the second longitudinal edge 18 if along more than about 70% of the width 19 of the elastic composite 10 is configured such that the first layer 20 is continuously not coupled to the second layer 22. In preferred embodiments, more than about 80% of the width 19 of the elastic composite 10 is configured such that the first layer 20 is continuously not coupled to the second layer 22. In even further preferable embodiments, more than about 90% of the width 19 of the elastic composite 10 is configured such that the first layer 20 is continuously not coupled to the second layer 22. Because of the independence of the first layer 20 with respect to the second layer 22 between the first longitudinal side edge 16 and the second longitudinal side edge 18, the first layer 20 can form gathers 36 in a direction parallel to the elastic composite longitudinal axis 12 when the elastic composite 10 is in a retracted condition, such as illustrated in FIGS. 3 and 4.

As depicted in FIG. 3, the gathers 36 formed in the first layer 20 can be greater in height and spacing as compared to the gathers 38 in the fourth layer 26 (only three gathers 38 are labeled in FIG. 3 for purposes of clarity). The gathers 36 in the first layer 20 can provide air gaps 40 that provide a benefit of cushion, and softness to the elastic composite 10. Additionally, the gathers 36 provide the benefit of the first layer 20 to be able to move with respect to the second layer 22, thus providing less friction if the elastic composite 10 is configured in an article such that the first layer 20 can contact a surface, such as the skin of a wearer. The three-dimensional nature of the gathers 36 can also provide an appearance of softness, providing an additional benefit for the elastic composite 10. Yet another advantage of the gathers 36 in the first layer 20 of the elastic composite 10 is increased opacity, due to the air gaps 40 and increased thickness of the elastic composite 10 providing more light diffraction.

Figure 5B:
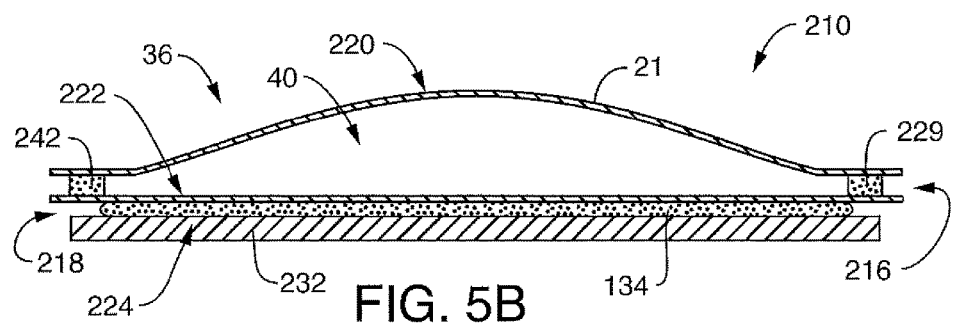
FIG. 5B is a cross-sectional view similar to FIG. 4, but of another alternative embodiment of an elastic composite in a retracted configuration.
Figure 6:
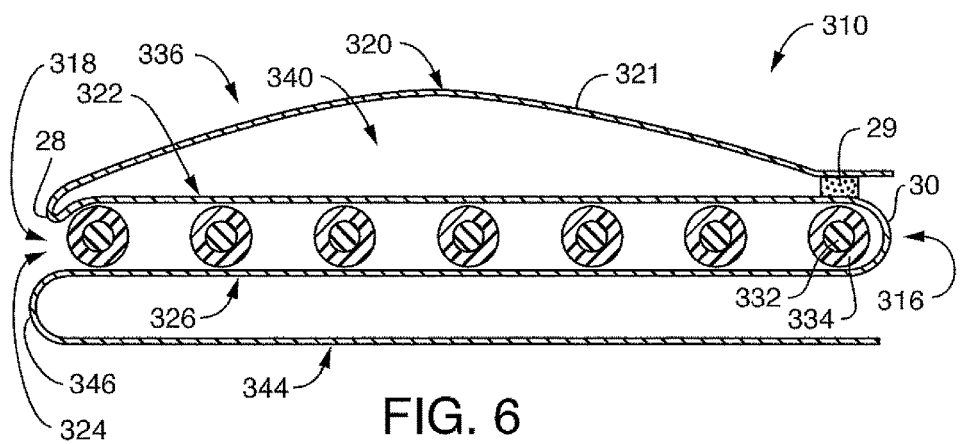
FIG. 6 is a cross-sectional view similar to FIG. 4, but of yet another alternative embodiment of an elastic composite in a retracted configuration.

FIGS. 5A-6 provide alternative embodiments of elastic composites 110, 210, 310 being shown in a cross-sectional view in a retracted configuration similar to the elastic composite 10 shown in FIG. 4. The elastic composites 110, 210, 310 in FIGS. 5A-6 have many similarities to the elastic composite 10 described above and depicted in FIGS. 1-4, so unless otherwise noted, the description above for the elastic composite 10 applies to the discussion of the elastic composites 110, 210, 310 below.

The elastic composite 110 depicted in FIG. 5A includes a first layer 120, a second layer 122, and a third layer 124. Unlike the elastic composite 10 described above, the third layer 124 in the elastic composite 110 is not disposed between a second layer 122 and a fourth layer. In some embodiments, the third layer 124 can include an elastic material 132. In the embodiment depicted in 5A, the elastic material 132 can be an elastic film. The elastic film of the third layer 124 can extend from substantially the first longitudinal edge 116 to the second longitudinal edge 118. The third layer 124 can be coupled to the second layer 122 with adhesive 134.

The elastic composite 210 of FIG. 5B is similar to the elastic composite 110 of FIG. 5A in that it can include a first layer 220, a second layer 222, a third layer 224, but no fourth layer as in the elastic composite 10 of FIGS. 1-4. The first layer 220 can be coupled to the second layer 222 at the first longitudinal edge 216 with adhesive 229 as described above with respect to the elastic composite 10 in FIGS. 1-4. The first layer 220 can be coupled to the second layer 222 at the second longitudinal edge 218 with adhesive 242. The configuration of having separate facing materials for the first layer 220 and the second layer 222 can provide advantages for the elastic composite 210. For example, the material selected to comprise the first layer 220 can be selected to have various properties that may be desired for an outer facing layer that may not be as necessary for the second layer 222. For example, the facing material comprising the first layer 220 can be a softer and thicker facing material as compared to the facing material of second layer 222. This can result in providing desired benefits for the first layer 220, while reducing cost of the second layer 222. Of course, it is contemplated that having one or more layers be separate from one another and coupled together can be applied to other embodiments of elastic composites 10, 110, 310 described herein, including for layers other than the first layer and second layer.

FIG. 6 provides another alternative embodiment of an elastic composite 310. The elastic composite 310 can include a first layer 320, a second layer 322, a third layer 324, and a fourth layer 326 similar to the elastic composite 10 described above and depicted in FIGS. 1-4. The elastic composite 310 can include a fifth layer 344. In some embodiments, the fifth layer 344 can comprise the same facing material as the first layer 320, the second layer 322, and the fourth layer 326. The fifth layer 344 can be coupled to the fourth layer 326 at the second longitudinal edge 318 of the elastic composite 310. As depicted in FIG. 6, in some embodiments, the fifth layer 344 can be coupled to the fourth layer 326 at the second longitudinal edge 318 of the elastic composite 310 with a fold 346. As discussed above with respect to other embodiments, it can be appreciated that the fifth layer 344 could be a separate material than the fourth layer 326, and coupled to the fourth layer 326 via various types of bonding. The fifth layer 344 can be independent of the fourth layer 346 at the first longitudinal edge 316 of the elastic composite 310. In some embodiments, the fifth layer 344 can be independent of the fourth layer from substantially the second longitudinal edge 318 of the elastic composite 310 to the first longitudinal edge 316 of the elastic composite 310. Such a configuration allows the fourth layer 326 to move independent of the fifth layer 344, as will be discussed in further detail below.

In the embodiments of the elastic composites 10, 110, 210, 310 described above, various materials can be utilized. In some embodiments, the facing materials that can be used to form the first layer 20, 120, 220, 320, the second layer 22, 122, 222, 322, the fourth layer 26, 326, and the fifth layer 344 can be a spunbond-meltblown-spunbond ("SMS") material. In some embodiments, the facing materials that can be used to form the first layer 20, 120, 220, 320, the second layer 22, 122, 222, 322, the fourth layer 26, 326, and the fifth layer 344 can be a spunbond material. It is also contemplated that the facing material could be comprised of other materials including, but not limited to, a spunbond-film-spunbond ("SFS"), a bonded carded web ("BCW"), or any non-woven material or woven material. In some embodiments, the facing material could be nylon, rayon, mesh materials, and/or film, among others. In some embodiments, the facing material could be comprised of a laminate of more than one of these exemplary materials, or other materials. In some embodiments, the facing material that can form one or more of the first layer 20, 120, 220, 320, the second layer 22, 122, 222, 322, the fourth layer 26, 326, and the fifth layer 344 can be comprised of a liquid impermeable material. In some embodiments, facing material(s) can be comprised of a material coated with a hydrophobic coating. The basis weight of the facing material can vary, however, in a preferred embodiment, the basis weight can be between about 8 gsm to about 120 gsm, not including the elastic members 32 in the waist containment member 84. More preferably, the basis weight of the material comprising the waist containment member 84 can be between about 10 gsm to about 40 gsm, and even more preferably, between about 15 gsm to about 25 gsm. Of course, it is contemplated that the basis weight of the facing material can be outside of these exemplary ranges in some embodiments and still be within the scope of this disclosure.

A wide variety of materials may be used for the elastic material 32, 132, 232, 332 in the elastic composite 10, 110, 210, 310. Suitable elastic materials 32, 132, 232, 332 can include sheets, strands or ribbons of natural rubber, synthetic rubber, elastic foams, or thermoplastic elastomeric materials (e.g., films), or any other suitable material exhibiting elastic properties. The elastic materials 32, 132, 232, 332 can be stretched and secured to the second layer 22, 122, 222, 322 and/or the fourth layer 26, 326 when forming the elastic composite 10, 110, 210, 310, secured to a gathered substrate such as the second layer 22, 122, 222, 322 and/or the fourth layer 26, 326, or secured to a substrate such as the second layer 22, 122, 222, 322 and/or the fourth layer 26, 326 and then elasticized or shrunk, for example, with the application of heat, such that the elastic retractive forces are imparted to the substrate.

The elastic composites 10, 110, 210, 310 described above can be utilized for a variety of applications. For example, the elastic composites 10, 110, 210, 310 could be utilized in absorbent articles, clothing, coveralls, workwear, athletic apparel, surgical gowns, etc. In clothing or apparel, the elastic composites 10, 110, 210, 310 can be useful in forming cuffs on sleeves, leg openings, or neck openings on garments. More discussion with potential uses of the elastic composites 10, 110, 210, 310 with respect to absorbent articles is described below.

Figure 7:
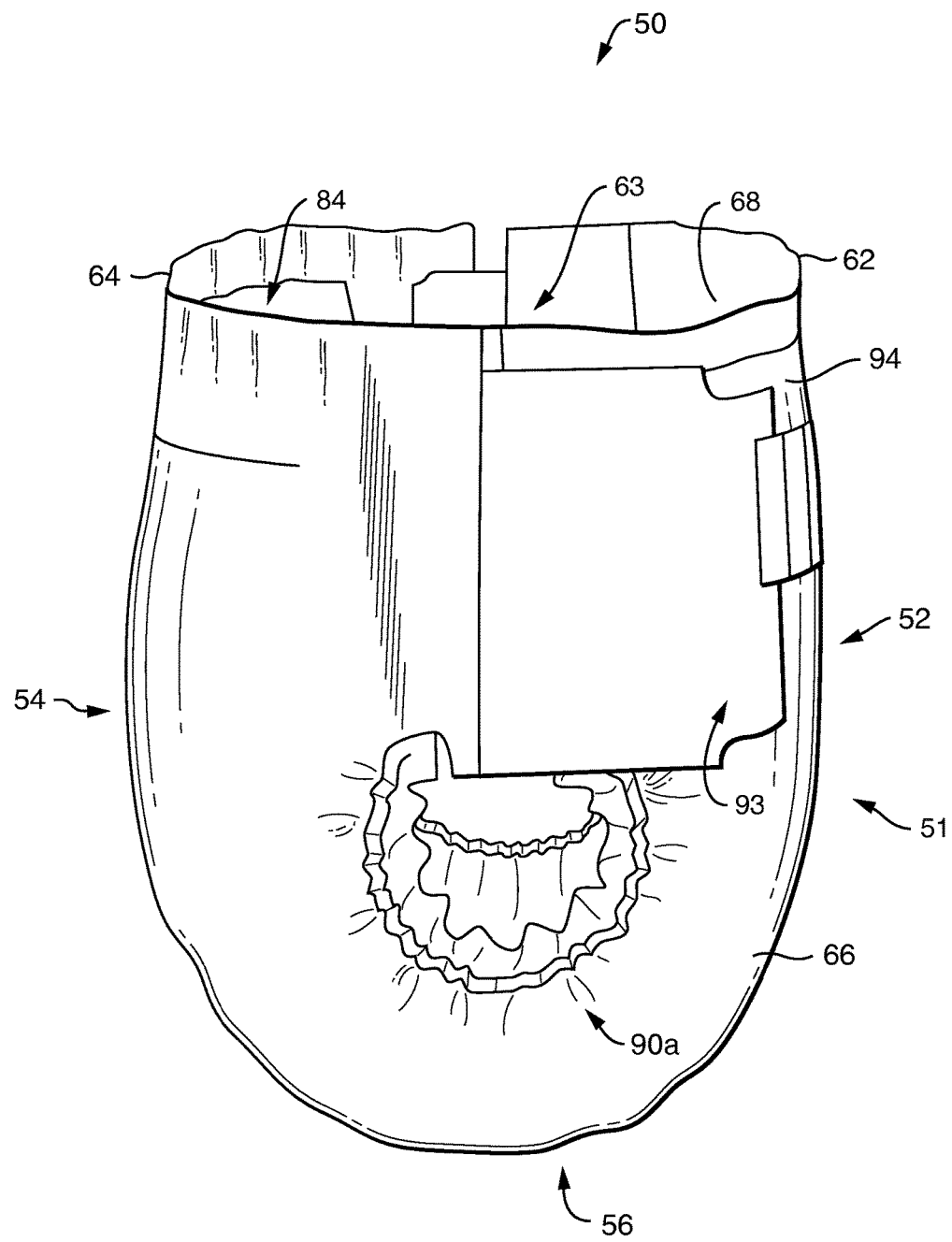
FIG. 7 is a side perspective view of an exemplary embodiment of an absorbent article, such as a diaper, in a fastened condition.
Figure 8:
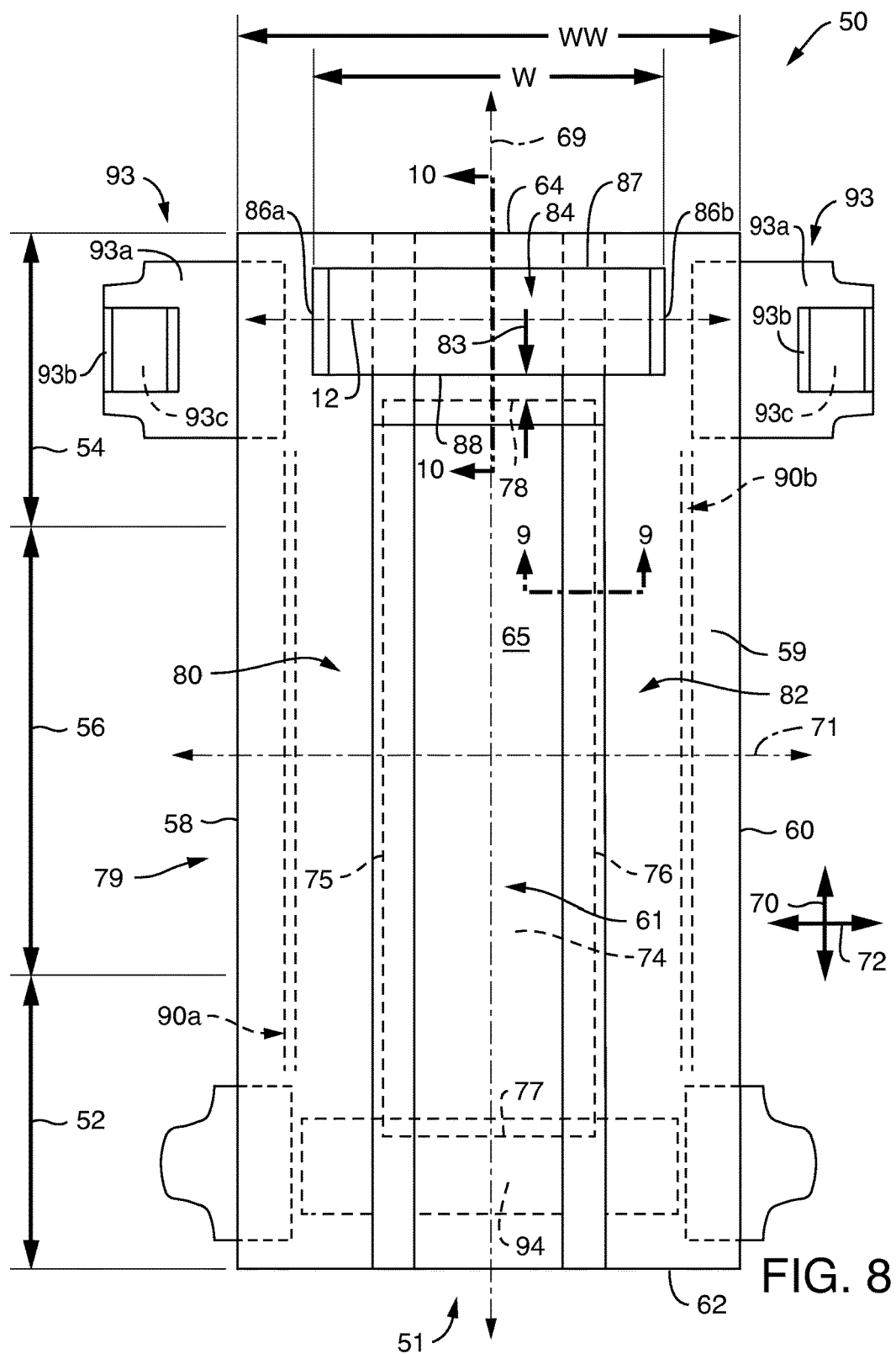
FIG. 8 is a top plan view of the absorbent article of FIG. 7 in a stretched, laid flat, unfastened condition.

Absorbent Article:

Referring to FIGS. 7 and 8, a non-limiting illustration of absorbent article 50, for example, a diaper, is illustrated. Other embodiments of the absorbent article could include training pants, youth pants, adult incontinence garments, and feminine hygiene articles. For example, a non-limiting illustration of an absorbent article 250, such as a training pant, is illustrated in FIG. 13. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 150 in FIGS. 11 and 12 provides an exemplary embodiment of an absorbent article 150 that can be manufactured in a cross-direction manufacturing process.

Figure 11:
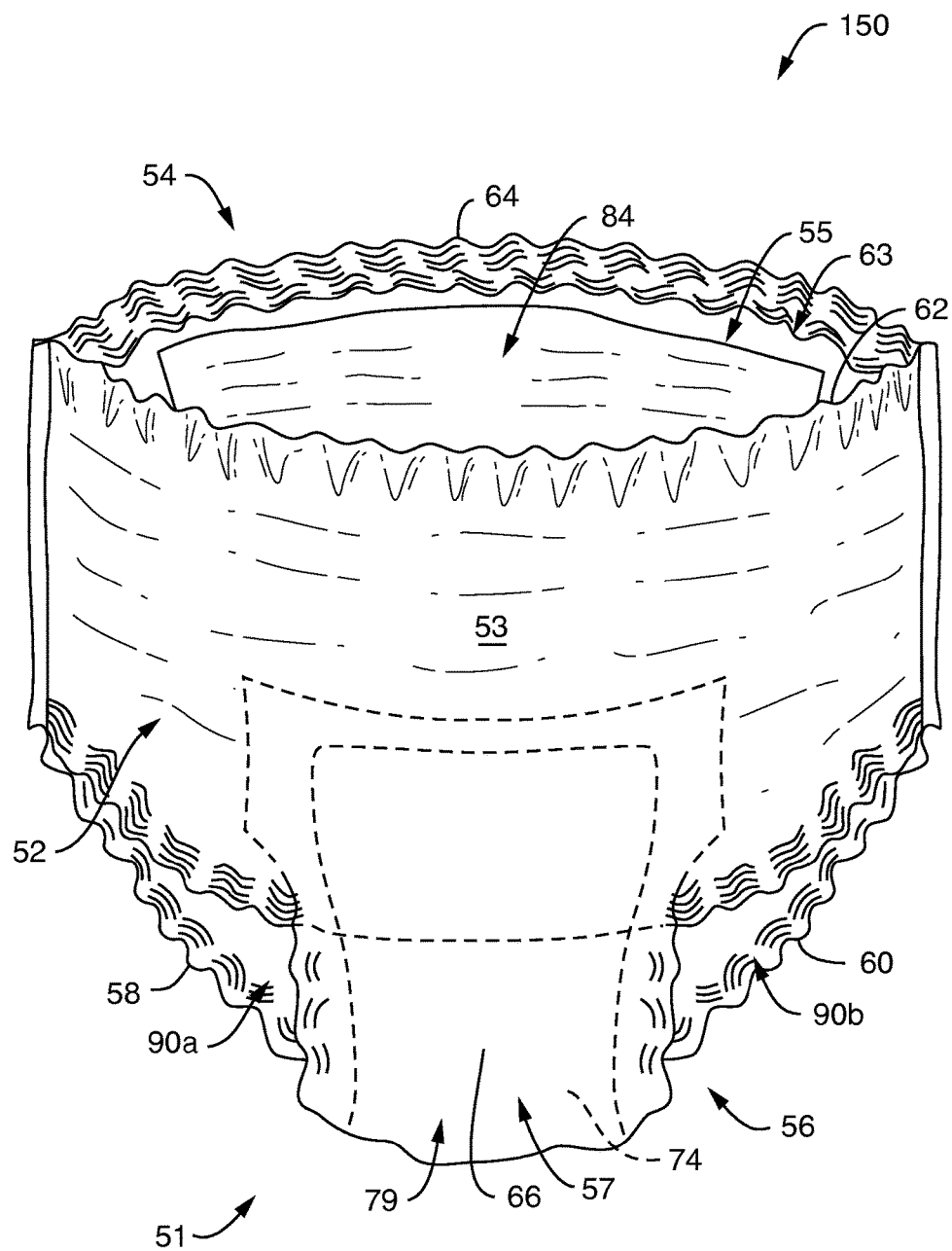
FIG. 11 is a front perspective view of an alternative embodiment of an absorbent article, such as a pant.
Figure 12:
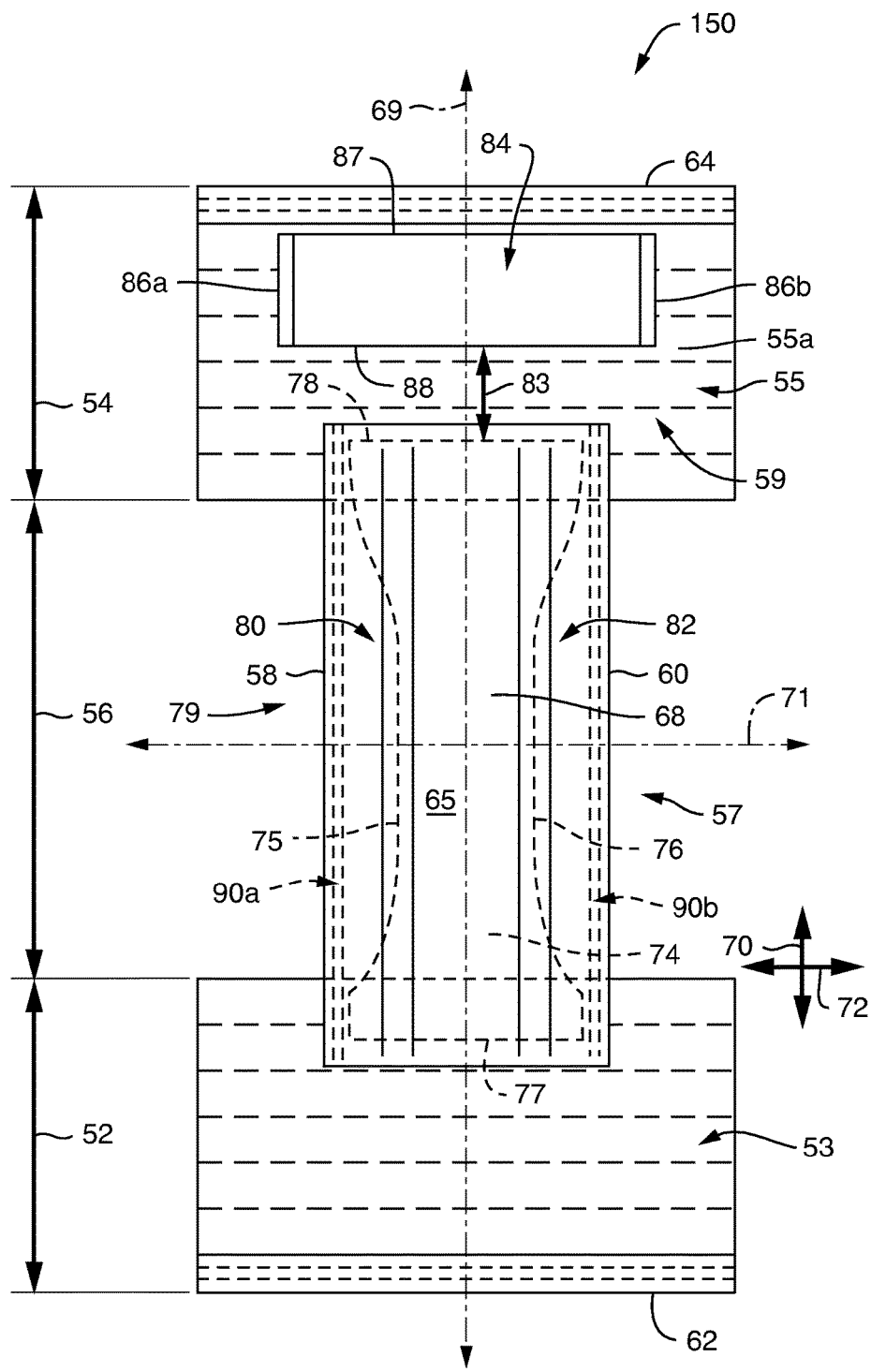
FIG. 12 is a top plan view of the absorbent article of FIG. 11 in a stretched, laid flat condition.
Figure 13:
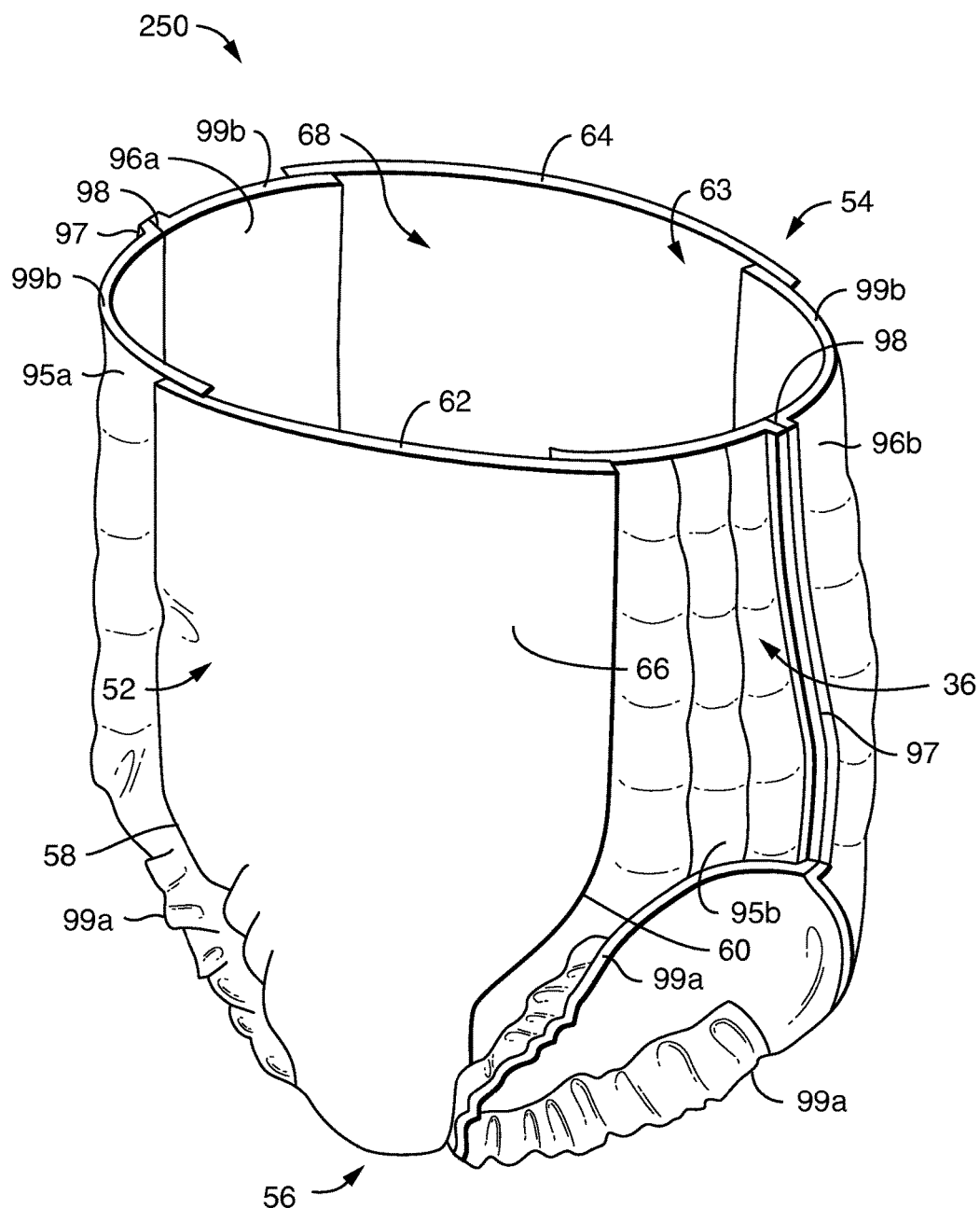
FIG. 13 is a front, side perspective view of another exemplary embodiment of an absorbent article, such as a pant, having side panels including an elastic composite.

The absorbent article 50 illustrated in FIGS. 7 and 8 and the absorbent article 150 in FIGS. 11 and 12 can each include a chassis 51. The absorbent article 50, 150 can include a front waist region 52, a rear waist region 54, and a crotch region 56 disposed between the front waist region 52 and the rear waist region 54 and interconnecting the front and rear waist regions, 52, 54, respectively. The front waist region 52 can be referred to as the front end region, the rear waist region 54 can be referred to as the rear end region, and the crotch region 56 can be referred to as the intermediate region. In the embodiment depicted in FIGS. 11 and 12, a three-piece construction of an absorbent article 150 is depicted where the absorbent article 150 can have a chassis 51 including a front waist panel 53 defining the front waist region 52, a rear waist panel 55 defining the rear waist region 54, and an absorbent panel 57 defining the crotch region 56 of the absorbent article 150. The absorbent panel 57 can extend between the front waist panel 53 and the rear waist panel 55. In some embodiments, the absorbent panel 57 can overlap the front waist panel 53 and the rear waist panel 55. The absorbent panel 57 can be bonded to the front waist panel 53 and the rear waist panel 55 to define a three-piece construction. However, it is contemplated that an absorbent article can be manufactured in a cross-direction without being a three-piece construction garment.

The absorbent article 50, 150 can have a pair of longitudinal side edges 58, 60, and a pair of opposite waist edges, respectively designated front waist edge 62 and rear waist edge 64. The front waist region 52 can be contiguous with the front waist edge 62 and the rear waist region 54 can be contiguous with the rear waist edge 64. The longitudinal side edges 58, 60 can extend from the front waist edge 62 to the rear waist edge 64. The longitudinal side edges 58, 60 can extend in a direction parallel to the longitudinal direction 70 for their entire length, such as for the absorbent articles 50, 150 illustrated in FIGS. 8 and 12. In other embodiments, the longitudinal side edges 58, 60 can be curved between the front waist edge 62 and the rear waist edge 64. In the absorbent article 150 of FIGS. 10 and 11, the longitudinal side edges 58, 60 can include portions of the front waist panel 53, the absorbent panel 57, and the rear waist panel 55.

The front waist region 52 can include the portion of the absorbent article 50, 150, 250 that, when worn, is positioned at least in part on the front of the wearer while the rear waist region 54 can include the portion of the absorbent article 50, 150, 250 that, when worn, is positioned at least in part on the back of the wearer. The crotch region 56 of the absorbent article 50, 150, 250 can include the portion of the absorbent article 50, 150, 250 that, when worn, is positioned between the legs of the wearer and can partially cover the lower torso of the wearer. The waist edges, 62 and 64, of the absorbent article 50, 150, 250 are configured to encircle the waist of the wearer and together define a central waist opening 63 (as labeled in FIGS. 7, 11, and 13) for the waist of the wearer. Portions of the longitudinal side edges 58, 60 in the crotch region 56 can generally define leg openings for the legs of the wearer when the absorbent article 50, 150, 250 is worn.

The absorbent article 50, 150 can include an outer cover 66 and a bodyside liner 68. The outer cover 66 and the bodyside liner 68 can form a portion of the chassis 51. In an embodiment, the bodyside liner 68 can be bonded to the outer cover 66 in a superposed relation by any suitable means such as, but not limited to, adhesives, ultrasonic bonds, thermal bonds, pressure bonds, or other conventional techniques. The outer cover 66 can define a length in a longitudinal direction 70, and a width in the lateral direction 72, which, in the illustrated embodiment of FIG. 7, can coincide with the length and width of the absorbent article 50. As illustrated in FIGS. 8 and 12, the absorbent article 50, 150 can have an absorbent article longitudinal axis 69 extending in the longitudinal direction 70 and an absorbent article lateral axis 71 extending in the lateral direction 72.

The chassis 51 can include an absorbent body 74. The absorbent body 74 can be disposed between the outer cover 66 and the bodyside liner 68. The absorbent body 74 can have longitudinal edges, 75 and 76, which, in an embodiment, can form portions of the longitudinal side edges, 58 and 60, respectively, of the absorbent article 50, 150. The absorbent body 74 can have a first end edge 77 that is opposite a second end edge 78, respectively, which, in an embodiment, can form portions of the waist edges, 62 and 64, respectively, of the absorbent article 50, 150. In some embodiments, the first end edge 77 can be in the front waist region 52. In some embodiments, the second end edge 78 can be in the rear waist region 54. In an embodiment, the absorbent body 74 can have a length and width that are the same as or less than the length and width of the absorbent article 50, 150. The bodyside liner 68, the outer cover 66, and the absorbent body 74 can form part of an absorbent assembly 79. In the absorbent article 150 of FIGS. 10 and 11, the absorbent panel 57 can form the absorbent assembly 79. The absorbent assembly 79 can also include a fluid transfer layer (not shown) and a fluid acquisition layer (not shown) between the bodyside liner 68 and the fluid transfer layer as is known by one of ordinary skill in the art. The absorbent assembly 79 can also include a spacer layer (not shown) disposed between the absorbent body 74 and the outer cover 66 as is known by one of ordinary skill in the art.

The absorbent article 50, 150 can be configured to contain and/or absorb liquid, solid, and semi-solid body exudates discharged from the wearer. In some embodiments, containment flaps 80, 82 can be configured to provide a barrier to the lateral flow of body exudates. To further enhance containment and/or absorption of body exudates, the absorbent article 50, 150 can suitably include a waist containment member 84. In some embodiments, the waist containment member 84 can provide a containment pocket 85 for containing body exudates. The waist containment member 84 can be disposed in the rear waist region 54 of the absorbent article 50, 150 in some embodiments. Although not depicted herein, it is contemplated that the waist containment member 84 can be additionally or alternatively disposed in the front waist region 52 of the absorbent article 50, 150.

The waist containment member 84 can be disposed on the body facing surface 59 of the chassis 51 to help contain and/or absorb body exudates. In some embodiments, such as in the absorbent article 50 depicted in FIGS. 7-9B, the waist containment member 84 can be disposed on the body facing surface 61 of the absorbent assembly 79. In some embodiments, the waist containment member 84 can be disposed on the body facing surface 65 of the bodyside liner 68. In some embodiments, such as in the absorbent article 150 depicted in FIGS. 11 and 12, the waist containment member 84 can be disposed on the body facing surface 55a of the rear waist panel 55.

The absorbent article 50, 150 can further include leg elastic members 90a, 90b as are known to those skilled in the art. The leg elastic members 90a, 90b can be attached to the outer cover 66 and/or the bodyside liner 68 along the opposite longitudinal side edges, 58 and 60, and positioned in the crotch region 56 of the absorbent article 50, 150. The leg elastic members 90a, 90b can be parallel to the absorbent article longitudinal axis 69 as shown in FIGS. 8 and 12 or can be curved as is known by one of ordinary skill in the art. The leg elastic members 90a, 90b can provide elasticized leg cuffs.

Additional details regarding each of these elements of the absorbent article 50, 150 described herein can be found below and with reference to the FIGS. 7 through 12.

Outer Cover:

The outer cover 66 and/or portions thereof can be breathable and/or liquid impermeable. The outer cover 66 and/or portions thereof can be elastic, stretchable, or non-stretchable. The outer cover 66 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 66 can be constructed of a microporous polymeric film, such as polyethylene or polypropylene. In some embodiments, the outer cover 66 can be formed by an elastic composite 10, 110, 210, 310 as discussed above and illustrated in FIGS. 1-6. In some embodiments, the front waist panel 53 and/or the rear waist panel 55 can be formed by an elastic composite 10, 110, 210, 310 as discussed above and illustrated in FIGS. 1-6.

In an embodiment, the outer cover 66 can be a single layer of a liquid impermeable material, such as a polymeric film. In an embodiment, the outer cover 66 can be suitably stretchable, and more suitably elastic, in at least the lateral direction 72 of the absorbent article 50, 150. In an embodiment, the outer cover 66 can be stretchable, and more suitably elastic, in both the lateral 72 and the longitudinal 70 directions. In an embodiment, the outer cover 66 can be a multi-layered laminate in which at least one of the layers is liquid impermeable. In some embodiments, the outer cover 66 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 66 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 66 can be a 20 gsm spunbond polypropylene non-woven web. In an embodiment, the outer layer may also be constructed of the same materials from which the bodyside liner 68 can be constructed as described herein.

The liquid impermeable inner layer of the outer cover 66 (or the liquid impermeable outer cover 66 where the outer cover 66 is of a single-layer construction) can be either vapor permeable (i.e., "breathable") or vapor impermeable. The liquid impermeable inner layer (or the liquid impermeable outer cover 66 where the outer cover 66 is of a single-layer construction) can be manufactured from a thin plastic film. The liquid impermeable inner layer (or the liquid impermeable outer cover 66 where the outer cover 66 is of a single-layer construction) can inhibit liquid body exudates from leaking out of the absorbent article 50, 150 and wetting articles, such as bed sheets and clothing, as well as the wearer and caregiver.

In some embodiments, where the outer cover 66 is of a single layer construction, it can be embossed and/or matte finished to provide a more cloth-like texture or appearance. The outer cover 66 can permit vapors to escape from the absorbent article 50, 150 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 74 can be suitably constructed to be generally compressible, conformable, pliable, non-irritating to the wearer's skin and capable of absorbing and retaining liquid body exudates. The absorbent body 74 can be manufactured in a wide variety of sizes and shapes (for example, rectangular, trapezoidal, T-shape, I-shape, hourglass shape, etc.) and from a wide variety of materials. The size and the absorbent capacity of the absorbent body 74 should be compatible with the size of the intended wearer (infants to adults) and the liquid loading imparted by the intended use of the absorbent article 50, 150, 250. The absorbent body 74 can have a length and width that can be less than or equal to the length and width of the absorbent article 50, 150, 250.

In an embodiment, the absorbent body 74 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 74 can be a matrix of cellulosic fluff and superabsorbent material. In an embodiment, the absorbent body 74 may be constructed of a single layer of materials, or in the alternative, may be constructed of two or more layers of materials.

Various types of wettable, hydrophilic fibers can be used in the absorbent body 74. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 74 can be free of superabsorbent material.

If a spacer layer is present, the absorbent body 74 can be disposed on the spacer layer and superposed over the outer cover 66. The spacer layer can be bonded to the outer cover 66, for example, by adhesive. In some embodiments, a spacer layer may not be present and the absorbent body 74 can directly contact the outer cover 66 and can be directly bonded to the outer cover 66. However, it is to be understood that the absorbent body 74 may be in contact with, and not bonded with, the outer cover 66 and remain within the scope of this disclosure. In an embodiment, the outer cover 66 can be composed of a single layer and the absorbent body 74 can be in contact with the singer layer of the outer cover 66. In some embodiments, at least a portion of a layer, such as but not limited to, a fluid transfer layer and/or a spacer layer, can be positioned between the absorbent body 74 and the outer cover 66. The absorbent body 74 can be bonded to the fluid transfer layer and/or the spacer layer.

Bodyside Liner:

The bodyside liner 68 of the absorbent article 50, 150, 250 can overlay the absorbent body 74 and the outer cover 66 and can isolate the wearer's skin from liquid waste retained by the absorbent body 74. In various embodiments, a fluid transfer layer (not shown) can be positioned between the bodyside liner 68 and the absorbent body 74. In various embodiments, an acquisition layer (not shown) can be positioned between the bodyside liner 68 and the absorbent body 74 or a fluid transfer layer, if present. In various embodiments, the bodyside liner 68 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 68 can extend beyond the absorbent body 74 and/or a fluid transfer layer, if present, and/or an acquisition layer, if present, and/or a spacer layer, if present, to overlay a portion of the outer cover 66 and can be bonded thereto by any method deemed suitable, such as, for example, by being bonded thereto by adhesive, to substantially enclose the absorbent body 74 between the outer cover 66 and the bodyside liner 68. The bodyside liner 68 may be narrower than the outer cover 66. However, in other embodiments, the bodyside liner 68 and the outer cover 66 may be of the same dimensions in width and length. In other embodiments, the bodyside liner 68 can be of greater width than the outer cover 66. It is also contemplated that the bodyside liner 68 may not extend beyond the absorbent body 74 and/or may not be secured to the outer cover 66. In some embodiments, the bodyside liner 68 can wrap at least a portion of the absorbent body 74, including wrapping around both longitudinal edges 75, 76 of the absorbent body 74, and/or one or more of the end edges 77, 78. It is further contemplated that the bodyside liner 68 may be composed of more than one segment of material. The bodyside liner 68 can be of different shapes, including rectangular, hourglass, or any other shape. The bodyside liner 68 can be suitably compliant, soft feeling, and non-irritating to the wearer's skin and can be the same as or less hydrophilic than the absorbent body 74 to permit body exudates to readily penetrate through to the absorbent body 74 and provide a relatively dry surface to the wearer.

The bodyside liner 68 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 68. The bodyside liner 68 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 68 need not be a unitary layer structure, and thus, can include more than one layer of fabrics, films, and/or webs, as well as combinations thereof. For example, the bodyside liner 68 can include a support layer and a projection layer that can be hydroentagled. The projection layer can include hollow projections, such as those disclosed in U.S. Patent Application Publication No. 2014/0121623 invented by Kirby, Scott S. C. et al.

For example, the bodyside liner 68 can be composed of a meltblown or spunbond web of polyolefin fibers. Alternatively, the bodyside liner 68 can be a bonded-carded web composed of natural and/or synthetic fibers. The bodyside liner 68 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 68 or it can be selectively applied to particular sections of the bodyside liner 68.

In an embodiment, a bodyside liner 68 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 68 can be a spunbond substrate with a basis weight from about 10 or 12 to about 15 or 20 gsm. In an embodiment, a bodyside liner 68 can be a 12 gsm spunbond-meltblown-spunbond substrate having 10% meltblown content applied between the two spunbond layers.

Although the outer cover 66 and bodyside liner 68 can include elastomeric materials, it is contemplated that the outer cover 66 and the bodyside liner 68 can be composed of materials which are generally non-elastomeric. In an embodiment, the bodyside liner 68 can be stretchable, and more suitably elastic. In an embodiment, the bodyside liner 68 can be suitably stretchable and more suitably elastic in at least the lateral or circumferential direction of the absorbent article 50, 150. In other aspects, the bodyside liner 68 can be stretchable, and more suitably elastic, in both the lateral and the longitudinal directions 72, 70, respectively.

Containment Flaps:

In an embodiment, the absorbent article 50, 150, 250 can include a pair of containment flaps 80, 82 (shown in FIGS. 8 and 12). The containment flaps 80, 82 can be formed separately from the absorbent chassis 51 and attached to the chassis 51 or can be formed integral to the chassis 51. In some embodiments, the containment flaps 80, 82 can be secured to the chassis 51 of the absorbent article 50, 150, 250 in a generally parallel, spaced relation with each other laterally inward of the leg openings to provide a barrier against the flow of body exudates. One containment flap 80 can be on a first side of the absorbent article longitudinal axis 69 and the other containment flap 82 can be on a second side of the absorbent article longitudinal axis 69. In an embodiment, the containment flaps 80, 82 can extend generally in a longitudinal direction 70 from the front waist region 52 of the absorbent article 50, 150, 250 through the crotch region 56 to the rear waist region 54 of the absorbent article 50, 150, 250. In some embodiments, the containment flaps 80, 82 can extend in a direction substantially parallel to the absorbent article longitudinal axis 69 of the absorbent article 50, 150, 250, however, in other embodiments, the containment flaps 80, 82 can be curved, as is known by one of ordinary skill in the art. In other embodiments, such as the absorbent article 150 in FIGS. 11 and 12, the containment flaps 80, 82 can be disposed on the absorbent panel 57.

In embodiments where the containment flaps 80, 82 are coupled to the chassis 51, the containment flaps 80, 82 can be bonded to the bodyside liner 68, the outer cover 66, or another layer, such as a spacer layer, if present, with a barrier adhesive 81 (as labeled in FIGS. 9A and 9B), as is known by one of ordinary skill in the art. Of course, the containment flaps 80, 82 can be bonded to other components of the chassis 51 and can be bonded with other suitable means other than a barrier adhesive 81. For example, the containment flaps 80, 82 can be bonded to the bodyside liner 68, the outer cover 66, or another layer with pressure bonding, thermal bonding, or ultrasonic bonding. The containment flaps 80, 82 can be constructed of a fibrous material which can be similar to the material forming the bodyside liner 68. Other conventional materials, such as polymer films, can also be employed. As will be discussed in more detail below, one or more of the containment flaps 80, 82 can be configured as an elastic composite 10, 110, 210, 310 as previously described.

Figure 9A:
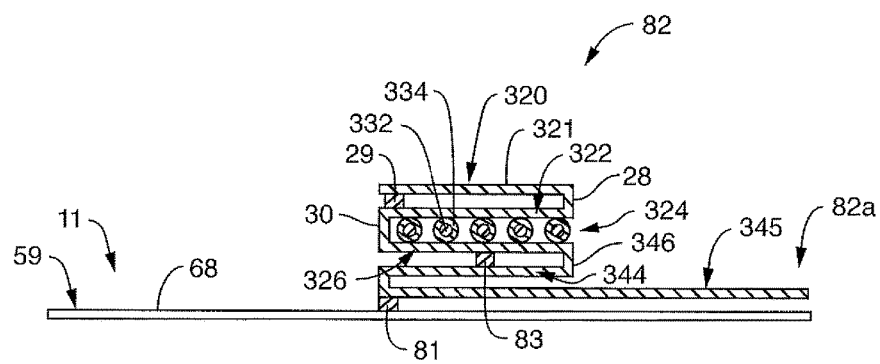
FIG. 9A is a cross-sectional view taken along line 9-9 from FIG. 8, illustrating an exemplary embodiment of a containment flap including an elastic composite.
Figure 9B:
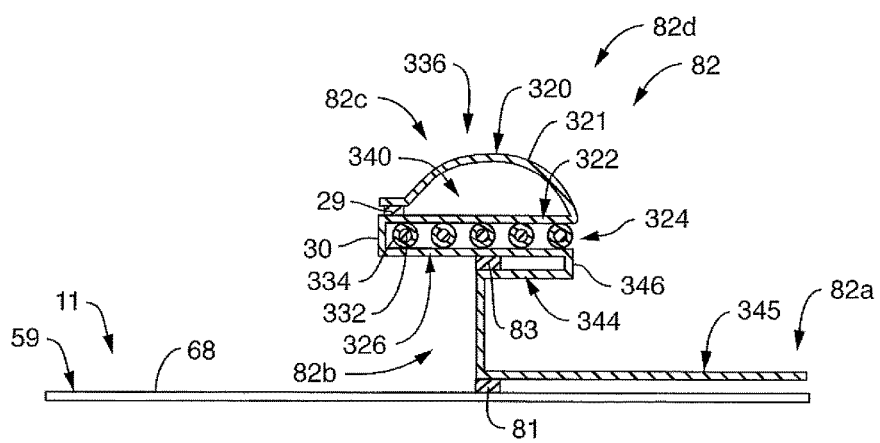
FIG. 9B is a cross-sectional view taken along line 9-9 from FIG. 8 similar to FIG. 9A, but with the absorbent article in a relaxed configuration such that the containment flap extends away from the chassis.

In one embodiment, the containment flaps 80, 82 can be constructed in a "T-shape" configuration, similar to that as described in U.S. patent application Ser. No. 13/900,134 by Robert L. Popp et al., which published as U.S. Patent Application Publication 2014/0350504. For example, FIGS. 12A and 12B provide a cross-section of containment flap 82 from absorbent article 50 in a "T-shape" configuration. FIG. 9A depicts the configuration of the containment flap 82 when the absorbent article 50 is in the stretched, laid-flat configuration. FIG. 9B depicts the configuration of the containment flap 82 when the absorbent article 50 is in a relaxed configuration. The containment flap 80 can be configured in a similar fashion as described herein for containment flap 82. The containment flap 82, as well as containment flap 80, can be configured similar to the elastic composite 310 as described above and illustrated in FIG. 6. As illustrated in FIG. 9B, the containment flap 82 can include a first layer 320, a second layer 322, a third layer 324, a fourth layer 326, and a fifth layer 344. The containment flap 82 can also include a sixth layer 345 disposed under the fifth layer 344 and coupled to the fifth layer 344. Similar to the discussion above regarding the elastic composite 310, the third layer 324 can include elastic materials 332 that are coupled by adhesive 334 (only one elastic material 332 and adhesive 334 labeled in FIGS. 9A and 9B for clarity) to the second layer 322 and the fourth layer 326. In one embodiment, the containment flap 82 can include five elastic materials 332. The elastic materials 332 can be coupled to the second layer 322 and the fourth layer 326 when the elastic materials 332 are in an elongated or extended configuration, for example, between about 110% to about 350% elongation. The elastic materials 332 can impart elastic characteristics to the containment flap 82, as will be discussed in further detail below. Of course, it is contemplated that the elastic materials 332 can be coupled to the second layer 322 and/or the fourth layer 324 in various other ways rather than adhesive 334 as known by those of skill in the art to provide the elastic characteristics to the containment flap 82.

The containment flap 82 can include a foot portion 82a and a stem portion 82b. The containment flap 82 can also include an inner flap 82c and an outer flap 82d (as labeled in FIG. 9B). The foot portion 82a can comprise the sixth layer 345 and can be bonded to the body facing surface 59 of the chassis 11 (e.g., bodyside liner 68). The fourth layer 346 can be coupled to the fifth layer 344 with adhesive 83 that can define an end to the stem portion 82b of the containment flap 82. The relaxing of the elastic materials 332 in containment flap 82 when the absorbent article 50 is in a relaxed condition can cause the containment flap 82 to gather and cause the stem portion 82 of the containment flap 82 to extend away from the body facing surface 59 of the chassis 51 (e.g., bodyside liner 68), as depicted in FIG. 9B. The gathers 336 formed in the first layer 322 and resultant air gaps 340 can provide increased softness to the outer surface 321 that can contact a wearer's skin. The gathers 336 can also provide an increased perception of softness for the containment flaps 80, 82 when the absorbent article 50 is viewed by a wearer and/or caregiver.

FIGS. 9A and 9B present just one possible configuration of containment flaps 80, 82. It is contemplated that the containment flaps 80, 82 can be of various configurations and shapes, and can be constructed by various methods. It is contemplated that in some embodiments, the containment flaps 80, 82 include other embodiments of elastic composites 10, 110, 210. It is also contemplated that the absorbent article 50, 150, 250 need not include containment flaps 80, 82 and can still be within the scope of this disclosure.

Leg Elastics:

Leg elastic members 90a, 90b can be secured to the outer cover 66, such as by being bonded thereto by laminate adhesive, generally laterally inward of the longitudinal side edges, 58 and 60, of the absorbent article 50, 150. Leg elastic members 90, 90b can also be utilized in the absorbent article 250, such as a training pant, depicted in FIG. 13. The leg elastic members 90a, 90b can form elasticized leg cuffs that further help to contain body exudates. In an embodiment, the leg elastic members 90a, 90b may be disposed between inner and outer layers (not shown) of the outer cover 66 or between other layers of the absorbent article 50, for example, between the base portion 64 of each containment flap 80, 82 and the bodyside liner 68, between the base portion 64 of each containment flap 80, 82 and the outer cover 66, or between the bodyside liner 68 and the outer cover 66. The leg elastic members 90a, 90b can be one or more elastic components near each longitudinal side edge 58, 60. For example, the leg elastic members 90a, 90b as illustrated herein in FIGS. 8 and 12 each include two elastic strands. A wide variety of elastic materials may be used for the leg elastic members 90a, 90b. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 90a, 90b can be formed with the containment flaps 80, 82 and then attached to the chassis 51 in some embodiments. Of course, the leg elastic members 90a, 90b can be omitted from the absorbent article 50, 150 without departing from the scope of this disclosure.

Figure 10A:
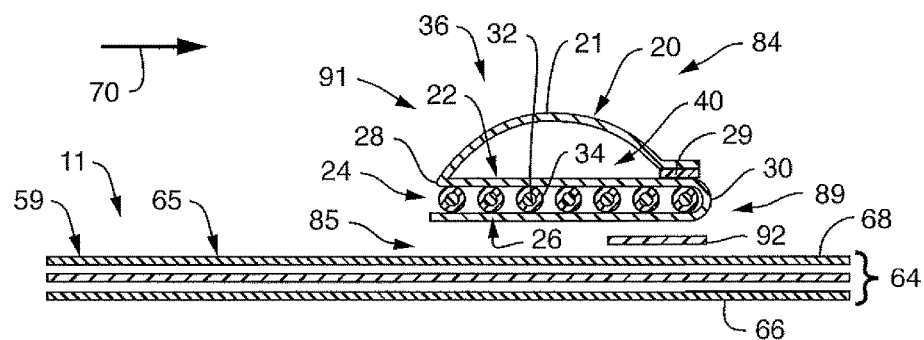
FIG. 10A is a cross-sectional view taken along line 10-10 from FIG. 8, illustrating an exemplary embodiment of a waist containment member including an elastic composite.
Figure 10B:
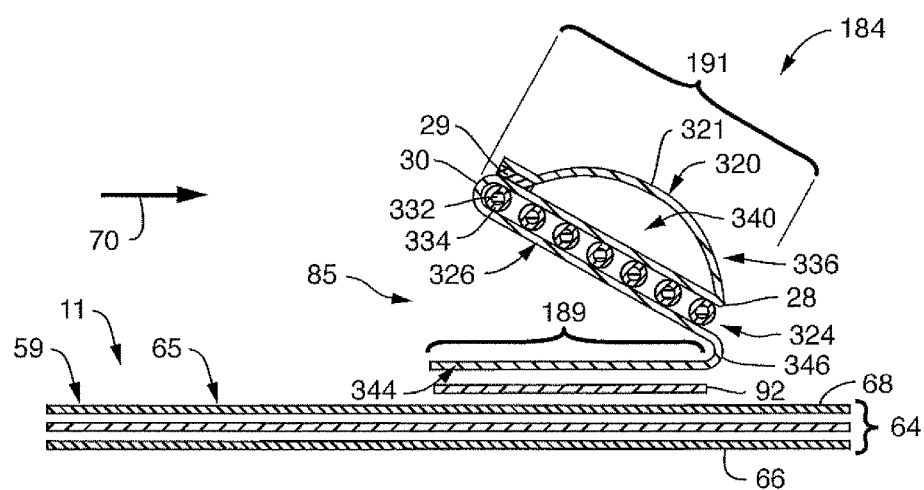
FIG. 10B is a cross-sectional view taken along line 10-10 from FIG. 8, but of an alternative embodiment of a waist containment member.

Waist Containment Member:

In an embodiment, the absorbent article 50, 150, 250 can have one or more waist containment members 84 (labeled in FIGS. 7, 8, 11, 12). FIGS. 8 and 10A illustrate a preferred embodiment of a waist containment member 84 on an absorbent article 50, such as a diaper. FIGS. 11 and 12 illustrate a preferred embodiment of a waist containment member 84 on an absorbent article 150, such as a pant. It is contemplated that the absorbent article 250 of FIG. 13 can include a waist containment member 84, as well. FIG. 10B illustrates an alternative embodiment of a waist containment member 184 that can be used with absorbent articles 50, 150, 250. Unless otherwise noted below, any discussion related to the waist containment member 84 for FIGS. 7, 8, 10A, 11, and 12 can apply to the waist containment member 184.

The waist containment member 84 can be disposed in the rear waist region 54. As will be discussed in more detail below, the waist containment member 84 can help contain and/or absorb body exudates, especially low viscosity fecal matter, and as such, can be preferred to be in the rear waist region 54. In some embodiments, the absorbent article 50, 150, 250 can have a waist containment member 84 disposed in the front waist region 52. A waist containment member 84 in the front waist region 52 can help contain and/or absorb body exudates, such as urine, in the front waist region 52. Although not as prevalent as in the rear waist region 54, in some circumstances, fecal material may also spread to the front waist region 52, and thus, a waist containment member 84 disposed in the front waist region 52 can help contain and/or absorb body exudates as well. In other embodiments, the absorbent article 50, 150, 250 can have a waist containment member 84 in both the rear waist region 54 and the front waist region 52.

The waist containment member 84 can be disposed on the body facing surface 61 of the absorbent assembly 79. In some embodiments, such as in embodiments illustrated in FIGS. 8, 10A, and 10B, the waist containment member 84 can be disposed on the body facing surface 65 of the bodyside liner 68. However, in some embodiments, such as the absorbent article 150 in FIG. 12, the waist containment member 84 can be disposed on a body facing surface 55a of the rear waist panel 55.

The waist containment member 84 can include a first longitudinal side edge 86a and a second longitudinal side edge 86b. The first longitudinal side edge 86a can be opposite from the second longitudinal side edge 86b. The distance between the first longitudinal side edge 86a and the second longitudinal side edge 86b can define a width W of the waist containment member 84 in the lateral direction 72, as shown in FIG. 8. Although not depicted, in some embodiments, the first longitudinal side edge 86a can substantially align with the first longitudinal side edge 58 of the absorbent article 50, 150. Similarly, in some embodiments, the second longitudinal side edge 86b can align with the second longitudinal side edge 60 of the absorbent article 50, 150. The waist containment member 84 can also include an upper lateral edge 87 and a lower lateral edge 88. The first longitudinal side edge 86a, the second longitudinal side edge 86b, the upper lateral edge 87, and the lower lateral edge 88 are defined when the absorbent article 50, 150 is in the stretched, laid-flat configuration, such as illustrated in FIGS. 8 and 12.

In some embodiments, the width W of the waist containment member 84 in the lateral direction 72 as compared to the width WW of the chassis 51 (as labeled in FIG. 8) can have a ratio of about 0.85 to about 1.00, or about 0.87 to about 1.00, or about 0.90 to about 1.00. For purposes herein, the width WW of the chassis 51 for use in this ratio is the width of the chassis 51 in the waist region in which the waist containment member 84 is disposed and both width measurements are taken in a direction parallel to the lateral direction 72. Thus, for the examples illustrated herein, the width W of the waist containment member 84 can be compared to the width WW of the chassis 51 in the rear waist region 54. Additionally, the width W of the waist containment member 84 in the lateral direction 72 and the width WW of the chassis 51 as discussed for the ratios herein are to be measured when the absorbent article 50, 150 is in the stretched, laid flat configuration.

As best illustrated in FIG. 10A, the waist containment member 84 can be configured similar to the elastic composite 10 as described above and illustrated in FIGS. 1-4. The waist containment member 84 can be configured such that the elastic composite longitudinal axis 12 is substantially parallel to the absorbent article lateral axis 71 (as shown in FIG. 8). The waist containment member 10 can include a first layer 20, a second layer 22, a third layer 24, and a fourth layer 26. The third layer 24 can be comprised of elastic materials 32 (only one labeled in FIG. 10A for purposes of clarity). The elastic materials 32 forming the third layer 24 can be coupled to the first layer 20 and/or the fourth layer 26 with adhesive 34. In one embodiment, the waist containment member 84 can include seven elastic materials 32. The elastic materials 32 can be coupled to the second layer 22 and/or the fourth layer 26 when the elastic materials 32 are in an elongated or extended configuration, for example, between about 110% to about 350% elongation. The elastic materials 32 can impart elastic characteristics to the waist containment member 84. Of course, it is contemplated that the elastic materials 32 can be coupled to the second layer 22 and/or the fourth layer 24 in various other ways rather than adhesive 34 as known by those of skill in the art to provide the elastic characteristics to the waist containment member 84.

The waist containment member 84 can include a proximal portion 89 and a distal portion 91. The proximal portion 89 can be coupled to the body facing surface 59 of chassis 51 (e.g., the body facing surface 61 of the absorbent assembly 79 or the body facing surface 65 of the bodyside liner 68). For example, the proximal portion 89 can be coupled to the bodyside liner 28 in FIG. 10A by adhesive 92. In other embodiments, such as in the absorbent article 150 of FIGS. 11 and 12, the proximal portion 89 can be coupled to the body facing surface 55a of the rear waist panel 55. Of course, it is contemplated that the proximal portion 89 of the waist containment member 84 can be coupled to the chassis 11 using bonding means known by one of ordinary skill in the art other than adhesive 92. The distal portion 91 and can be free to move independent of the body facing surface 59 of the chassis 51 to provide a containment pocket 85 for containing body exudates when the absorbent article 50 is in a relaxed configuration. The containment pocket 85 can be especially beneficial for containing and/or absorbing low viscosity fecal matter, which can be prevalent in younger children.

As illustrated in FIG. 10A, when the absorbent article 50 is in a relaxed configuration, the first layer 20 can form gathers 36 and corresponding air gaps 40 as described above with respect to the elastic composite 10 and illustrated in FIGS. 1-4. Because the outer surface 21 can contact a wearer's skin, the gathers 36 and air gaps 40 can provide increased softness against the wearer's skin. The first layer 20 can move independent of the second layer 22 to also reduce friction against the wearer's skin. Additionally, the gathers 36 provide a perception of softness to the wearer and/or caregiver when viewing the absorbent article 50. Another benefit for the waist containment member 84 illustrated in FIG. 10A is that the gathers 36 and air gaps 40 can provide increased opacity to the waist containment member 84. The increased opacity can help cover the sight of body exudates that can be contained within the containment pocket 85.

FIG. 10B illustrates an alternative embodiment of a waist containment member 184, where the absorbent article to which it is coupled is in a relaxed configuration similar to FIG. 10A. The waist containment member 184 can be configured similar to the elastic composite 310 as discussed above and illustrated in FIG. 6. The waist containment member 184 can include a first layer 320, a second layer 322, a third layer 324, a fourth layer 326, and a fifth layer 344. The third layer 324 can include at least one elastic material 332. In the embodiment depicted in FIG. 10B, the third layer 324 can include seven elastic materials 332. The elastic materials 332 (only one labeled for clarity purposes) of the third layer 324 can be coupled to the second layer 322 and/or the fourth layer 326 with adhesive 334. As discussed above with respect to FIG. 10A, the elastic materials 332 can be coupled to the second layer 322 and/or the fourth layer 326 when the elastic materials 332 are in an elongated or extended configuration, for example, between about 110% to about 350% elongation, to impart elastic characteristics to the waist containment member 184. It is to be noted that in some embodiments, the fifth layer 344 can have a shorter length in the longitudinal direction 70 than the fourth layer 326.

The waist containment member 184 can include a proximal portion 189 coupled to the body facing surface 59 of the chassis 11 (e.g., body facing surface 65 of the bodyside liner 68). In other embodiments, such as in the absorbent article 150 of FIGS. 11 and 12, the proximal portion 189 can be coupled to the body facing surface 55a of the rear waist panel 55. As illustrated in FIG. 10B, the proximal portion 189 can comprise the fifth layer 189. The waist containment member 184 can also include a distal portion 191. The distal portion 191 can be formed by the first layer 320, the second layer 322, the third layer 324, and the fourth layer 326. The fold 346 that couples the fourth layer 326 to the fifth layer 344 can separate the proximal portion 189 from the distal portion 191. As used in this context, the fold 346 separates the proximal portion 189 from the distal portion 191 in that the fold 346 defines a transition between the proximal portion 189 and the distal portion 191.

When the absorbent article 50 is in a relaxed configuration, the elastic material 332 in the waist containment member 184 can cause the distal portion 191 to extend away from the body facing surface 59 of the chassis 11 to open the containment pocket 85 for body exudates, as illustrated in FIG. 10B. The containment pocket 85 can be especially beneficial for containing and/or absorbing low viscosity fecal matter, which can be prevalent in younger children. When the absorbent article 50 is in the relaxed configuration, the first layer 320 can form gathers 336 and corresponding air gaps 340 as described above with respect to the elastic composite 310 and illustrated in FIG. 6. Because the outer surface 321 can contact a wearer's skin, the gathers 336 and air gaps 340 can provide increased softness against the wearer's skin. The first layer 320 can move independent of the second layer 322 to also reduce friction against the wearer's skin. Additionally, the gathers 336 provide a perception of softness to the wearer and/or caregiver when viewing the absorbent article 50. Another benefit for the waist containment member 184 illustrated in FIG. 10B is that the gathers 336 and air gaps 340 can provide increased opacity to the waist containment member 184. The increased opacity can help cover the presence of body exudates that can be contained within the containment pocket 85.

It is contemplated that the waist containment member 84, 184 could be alternatively configured with one or more configurations similar to the elastic composites 110, 210 discussed above and illustrated in FIGS. 5A and 5B.

As depicted in FIGS. 8 and 12, in some embodiments the waist containment member 84, 184 can be disposed on the body facing surface 59 of the chassis 51 such that a gap 83 is provided between the second end edge 78 of the absorbent body 74 and the lower lateral edge 88 of the waist containment member 84, 184. By providing a gap 83, the containment pocket 85 can have a greater void volume for body exudates. Additionally, it is believed that gap 83 can help body exudates enter the containment pocket 85 of the waist containment member 84, 184.

The waist containment member 84, 184 can be comprised of a variety of materials as described above with respect to the elastic composites 10, 110, 210, 310. In a preferred embodiment, the waist containment member 84, 184 can be comprised of a spunbond-meltblown-spunbond ("SMS") material. However it is contemplated that the waist containment member 84, 184 can be comprised of other materials including, but not limited to, a spunbond-film-spunbond ("SFS"), a bonded carded web ("BOW"), or any non-woven, or woven material. In some embodiments, the waist containment member 84, 184 can be comprised of a laminate of more than one of these exemplary materials, or other materials. In some embodiments, the waist containment member 84, 184 can be comprised of a liquid impermeable material. In some embodiments, the waist containment member 84, 184 can be comprised of a material coated with a hydrophobic coating. The basis weight of the material forming the waist containment member 84, 184 can vary, however, in a preferred embodiment, the basis weight can be between about 8 gsm to about 120 gsm, not including the elastic materials in the waist containment member 84, 184. More preferably, the basis weight of the material comprising the waist containment member 84, 184 can be between about 10 gsm to about 40 gsm, and even more preferably, between about 15 gsm to about 25 gsm.

Fastening System:

In an embodiment, the absorbent article 50 can include a fastening system. The fastening system can include one or more back fasteners 93 and one or more front fasteners 94. The embodiment shown in FIGS. 7 and 8 depict an embodiment with one front fastener 94. Portions of the fastening system may be included in the front waist region 52, rear waist region 54, or both.

The fastening system can be configured to secure the absorbent article 50 about the waist of the wearer in a fastened condition as shown in FIG. 7 and help maintain the absorbent article 50 in place during use. In an embodiment, the back fasteners 91 can include one or more materials bonded together to form a composite ear as is known by one of ordinary skill in the art. For example, the composite fastener may be composed of a stretch component 93a, a nonwoven carrier or hook base 93b, and a fastening component 93c, as labeled in FIG. 8. Although not depicted herein, in some embodiments the waist containment member 84, 184 can extend to and be coupled to the back fasteners 93.

Side Panels:

As illustrated in FIG. 13, in an embodiment in which the absorbent article 250 can be a training pant, youth pant, diaper pant, or adult absorbent pant, the absorbent article 250 may have front side panels, 95a and 95b, and rear side panels, 96a and 96b. The front side panels 95a, 95b and the rear side panels 96a, 96b of the absorbent article 250 can be bonded to the absorbent article 250 in the respective front and back waist regions, 52 and 54, and can extend outwardly beyond the longitudinal side edges, 58 and 60, of the absorbent article 250. In an example, the front side panels 95a, 95b can be bonded to the inner surface of the outer cover 66, such as being bonded thereto by adhesive, by pressure bonding, by thermal bonding or by ultrasonic bonding. These front side panels 95a, 95b may also be bonded to the outer surface of the outer cover 66, such as by being bonded thereto by adhesive, by pressure bonding, by thermal bonding, or by ultrasonic bonding. The back side panels 96a, 96b may be secured to the outer cover 66 at the back waist region 54 of the absorbent article 250 in substantially the same manner as the front side panels 95a, 95b. Alternatively, the front side panels 95a, 95b and the back side panels 96a, 96b may be formed integrally with the absorbent article 250, such as by being formed integrally with the outer cover 66, the bodyside liner 68, or other layers of the absorbent article 250. As illustrated in FIG. 16, the absorbent article 10 can include the containment flaps 44, 46 as discussed above. The containment flaps 44, 46 can be bonded to the body facing liner 28.

For improved fit and appearance, the front side panels 95a, 95b and the back side panels 96a, 96b can suitably have an average length measured parallel to the absorbent article longitudinal axis of that is about 20 percent or greater, and more suitably about 25 percent or greater, of the overall length of the absorbent article 250. For example, absorbent articles 1250 having an overall length of about 54 centimeters, the front side panels 95a, 95b and the back side panels 96a, 96b suitably have an average length of about 10 centimeters or greater, and more suitably have an average length of about 15 centimeters.

The front side panels 95a, 95b and the back side panels 96a, 96b can be comprised of a variety of materials. In some embodiments, at least one of the front side panels 95a, 95b and/or the back side panels 96a, 96b can be comprised of an elastic composite 10, 110, 210, 310 as described herein. In some embodiments, each of the front side panels 95a, 95b and the back side panels 96a, 96b can be comprised of an elastic composite 10, 110, 210, 310 as described herein. Each of the front side panels 95a, 95b and each of the back side panels 96a, 96b can be constructed of one or more individual, distinct pieces of material. For example, in FIG. 13, each of the front side panels 95a, 95b and each of the back side panels 96a, 96b is configured of one of the elastic composites 10, 110, 210, 310 described herein. The front side panels 95a, 95b and the back side panels 96a, 96b can have a puffy appearance due to the gathers 36 (only one labeled on front side panel 95b). The gathers 36 can provide a softer surface for the front side panels 95a, 95b and the back side panels 96a, 96b as well as an increased appearance of softness.

The front side panels 95a, 95b and back side panels 96a, 96b can each have an outer edge 97 spaced laterally from the engagement seam 98, a leg end edge 99a disposed toward the longitudinal center of the absorbent article 250, and a waist end edge 99b disposed toward a longitudinal end of the absorbent article 250. The leg end edge 99a and waist end edge 99b can extend from the longitudinal side edges 58, 60 of the absorbent article 250 to the outer edges. The leg end edges 99a of the front side panels 95a, 95b and back side panels 96a, 96b can form part of the longitudinal side edges 58, 60 of the absorbent article 250. The leg end edges 99a of the illustrated absorbent article 250 can be curved and/or angled relative to the transverse axis to provide a better fit around the wearer's legs. However, it is understood that only one of the leg end edges 99a can be curved or angled, such as the leg end edge 99a of the back waist region 54, or neither of the leg end edges 99a can be curved or angled, without departing from the scope of this disclosure. The waist end edges 99b can be parallel to the transverse axis. The waist end edges 99b of the front side panels 95a, 95b can form part of the front waist edge 62 of the absorbent article 250, and the waist end edges 99b of the back side panels 96a, 96b can form part of the back waist edge 64 of the absorbent article 250.

The front side panels 95a, 95b and the back side panels 96a, 96b can include an elastic material capable of stretching laterally. For example, the elastic material can be one of the elastic materials 32, 132, 232, 332 described above for the elastic composites 10, 110, 210, 310. The front side panels 95*a*, 95*b* and the back side panels 96*a*, 96*b* can also include other woven or non-woven materials, such as those described above as facing materials for the elastic composite 10, 110, 210, 310.

EMBODIMENTS

Embodiment 1

An elastic composite including an elastic composite longitudinal axis and an elastic composite lateral axis, the elastic composite comprising: a first longitudinal edge and a second longitudinal edge, the first longitudinal edge and the second longitudinal edge each extending in a direction generally parallel to the elastic composite longitudinal axis; a first layer formed by at least one facing material; a second layer formed by at least one facing material; and a third layer formed by at least one elastic material, the third layer being coupled to the second layer when the at least one elastic material is in an extended condition and the first layer being coupled to the second layer near the first longitudinal edge and the second longitudinal edge but being independent of the second layer therebetween such that when the elastic composite is in a retracted condition the first layer forms gathers in the direction parallel to the elastic composite longitudinal axis.

Embodiment 2

The elastic composite of embodiment 1, wherein the at least one facing material of the first layer is coupled to the at least one facing material of the second layer at the second longitudinal edge by a fold.

Embodiment 3

The elastic composite of any one of the preceding embodiments, further comprising a fourth layer, the fourth layer being formed by at least one facing material.

Embodiment 4

The elastic composite of embodiment 3, wherein the at least one elastic material is disposed between the second layer and the fourth layer.

Embodiment 5

The elastic composite of embodiment 4, wherein the at least one facing material of the second layer is coupled to the at least one facing material of the fourth layer at the first longitudinal edge by a fold.

Embodiment 6

The elastic composite of any one of embodiments 3-5, further comprising a fifth layer, the fifth layer comprising at least one facing material and being coupled to the fourth layer at the second longitudinal edge Embodiment 7

The elastic composite of embodiment 6, wherein the at least one facing material of the fifth layer is coupled to the at least one facing material of the fourth layer by a fold.

Embodiment 8

The elastic composite of any one of the preceding embodiments, further comprising a plurality of elastic materials, the plurality of elastic materials forming the third layer.

Embodiment 9

An absorbent article including a front waist region, a rear waist region, a crotch region, an absorbent article longitudinal axis and an absorbent article lateral axis, the absorbent article comprising: a chassis including an absorbent body, the chassis including a body facing surface; and an elastic composite, the elastic composite comprising: an elastic composite longitudinal axis and an elastic composite lateral axis; a first longitudinal edge and a second longitudinal edge, the first longitudinal edge and the second longitudinal edge each extending in a direction generally parallel to the elastic composite longitudinal axis; a first layer formed by at least one facing material; a second layer formed by at least one facing material; and a third layer formed by at least one elastic material, the third layer being coupled to the second layer when the at least one elastic material is in an extended condition and the first layer being coupled to the second layer near the first longitudinal edge and the second longitudinal edge but being independent of the second layer therebetween such that when the elastic composite is in a retracted condition the first layer forms gathers in the direction parallel to the longitudinal axis.

Embodiment 10

The absorbent article of embodiment 9, wherein the first layer includes an outer surface, the outer surface providing a body-facing surface for the absorbent article.

Embodiment 11

The absorbent article of embodiment 9 or embodiment 10, wherein the third layer is coupled to the body facing surface of the chassis when the at least one elastic material is in the extended condition such that when the elastic composite is in the retracted condition the elastic composite forms gathers.

Embodiment 12

The absorbent article of any one of embodiments 9-11, further comprising a waist containment member, the waist containment member being provided by the elastic composite and being configured such that the elastic composite longitudinal axis is substantially parallel to the absorbent article lateral axis.

Embodiment 13

The absorbent article of embodiment 12, wherein the elastic composite further comprises: a fourth layer, the fourth layer being coupled to the body facing surface of the chassis.

Embodiment 14

The absorbent article of embodiment 13, wherein the at least one elastic material is disposed between the second layer and the fourth layer.

Embodiment 15

The absorbent article of any one of embodiments 9-14, wherein the elastic composite further comprises a plurality of elastic materials, the plurality of elastic materials forming the third layer.

Embodiment 16

The absorbent article of embodiment 12, wherein the elastic composite further comprises: a fourth layer, the at least one elastic material being disposed between the second layer and the fourth layer; and a fifth layer, the fifth layer being coupled to the body facing surface of the chassis, and the fifth layer being coupled to the fourth layer at the second longitudinal edge but not at the first longitudinal edge such that the fourth layer can move independent of the fifth layer near the first longitudinal edge to form a containment pocket for containing exudates between the fourth layer and the fifth layer.

Embodiment 17

The absorbent article of embodiment 16, wherein the first layer, the second layer, the fourth layer, and the fifth layer comprise the same at least one facing material, the first layer is coupled to the second layer at the second longitudinal edge with a fold, the second layer is coupled to the fourth layer at the first longitudinal edge with a fold, and the fourth layer is coupled to the fifth layer at the second longitudinal edge with a fold.

Embodiment 18

The absorbent article of any one of embodiments 12-14, 16, or 17, wherein the waist containment member is in the rear waist region.

Embodiment 19

The absorbent article of any one of embodiments 9-11, further comprising: a pair of leg containment flaps, each of the leg containment flaps being comprised of an elastic composite.

Embodiment 20

The absorbent article of any one of embodiments 9-11, further comprising: at least one pair of side panels, each of the side panels being comprised of an elastic composite.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An elastic composite including an elastic composite longitudinal axis and an elastic composite lateral axis, the elastic composite comprising:
   a first longitudinal edge and a second longitudinal edge, the first longitudinal edge and the second longitudinal edge each extending in a direction generally parallel to the elastic composite longitudinal axis;
   a first layer formed by at least one facing material;
   a second layer formed by at least one facing material;
   a third layer formed by at least one elastic material, the third layer being coupled to the second layer when the at least one elastic material is in an extended condition and the first layer being coupled to the second layer at the first longitudinal edge and the second longitudinal edge but being independent of the second layer therebetween such that when the elastic composite is in a retracted condition the first layer forms gathers in the direction parallel to the elastic composite longitudinal axis; and
   a fourth layer, the fourth layer being formed by at least one facing material, wherein the third layer is disposed between the second layer and the fourth layer.

2. The elastic composite of claim 1, wherein the at least one facing material of the first layer is coupled to the at least one facing material of the second layer at the second longitudinal edge by a fold.

3. The elastic composite of claim 1, wherein the at least one facing material of the second layer is coupled to the at least one facing material of the fourth layer at the first longitudinal edge by a fold.

4. The elastic composite of claim 1, further comprising a fifth layer, the fifth layer comprising at least one facing material and being coupled to the fourth layer at the second longitudinal edge.

5. The elastic composite of claim 4, wherein the at least one facing material of the fifth layer is coupled to the at least one facing material of the fourth layer by a fold.

6. The elastic composite of claim 1, further comprising a plurality of elastic materials, the plurality of elastic materials forming the third layer.

7. An absorbent article including a front waist region, a rear waist region, a crotch region, an absorbent article longitudinal axis and an absorbent article lateral axis, the absorbent article comprising:
   a chassis including an absorbent body, the chassis including a body facing surface; and
   an elastic composite, the elastic composite comprising:
      an elastic composite longitudinal axis and an elastic composite lateral axis;
      a first longitudinal edge and a second longitudinal edge, the first longitudinal edge and the second longitudinal edge each extending in a direction generally parallel to the elastic composite longitudinal axis;
      a first layer formed by at least one facing material;
      a second layer formed by at least one facing material;
      a third layer formed by at least one elastic material, the third layer being coupled to the second layer when the at least one elastic material is in an extended condition and the first layer being coupled to the second layer at the first longitudinal edge and the second longitudinal edge but being independent of the second layer therebetween such that when the elastic composite is in a retracted condition the first layer forms gathers in the direction parallel to the longitudinal axis; and
- a fourth layer, the fourth layer being coupled to the body facing surface of the chassis, wherein the third layer is disposed between the second layer and the fourth layer.

8. The absorbent article of claim 7, wherein the first layer includes an outer surface, the outer surface providing a body-facing surface for the absorbent article.

9. The absorbent article of claim 7, wherein the third layer is coupled to the body facing surface of the chassis when the at least one elastic material is in the extended condition such that when the elastic composite is in the retracted condition the elastic composite forms gathers.

10. The absorbent article of claim 7, further comprising a waist containment member, the waist containment member being provided by the elastic composite and being configured such that the elastic composite longitudinal axis is substantially parallel to the absorbent article lateral axis.

11. The absorbent article of claim 7, wherein the elastic composite further comprises a plurality of elastic materials, the plurality of elastic materials forming the third layer.

12. The absorbent article of claim 10, wherein the elastic composite further comprises:
- a fifth layer, the fifth layer being coupled to the body facing surface of the chassis, and the fifth layer being coupled to the fourth layer at the second longitudinal edge but not at the first longitudinal edge such that the fourth layer can move independent of the fifth layer near the first longitudinal edge to form a containment pocket for containing exudates between the fourth layer and the fifth layer.

13. The absorbent article of claim 12, wherein the first layer, the second layer, the fourth layer, and the fifth layer comprise the same at least one facing material, the first layer is coupled to the second layer at the second longitudinal edge with a fold, the second layer is coupled to the fourth layer at the first longitudinal edge with a fold, and the fourth layer is coupled to the fifth layer at the second longitudinal edge with a fold.

14. The absorbent article of claim 10, wherein the waist containment member is in the rear waist region.

15. The absorbent article of claim 7, further comprising:
- a pair of leg containment flaps, each of the leg containment flaps being comprised of an elastic composite.

16. The absorbent article of claim 7, further comprising:
- at least one pair of side panels, each of the side panels being comprised of an elastic composite.

* * * * *